(12) United States Patent
Dröge et al.

(10) Patent No.: US 10,342,748 B2
(45) Date of Patent: Jul. 9, 2019

(54) STABLE DISPERSIONS

(71) Applicant: Symrise AG, Holzminden (DE)

(72) Inventors: Jörg Dröge, Bordenwerder (DE); Jörn Wiedemann, Holzminden (DE)

(73) Assignee: Symrise AG, Holzminden (DE)

(*) Notice: Subject to any disclaimer, the term of this patent is extended or adjusted under 35 U.S.C. 154(b) by 0 days.

(21) Appl. No.: 15/553,013

(22) PCT Filed: Feb. 14, 2016

(86) PCT No.: PCT/EP2016/053085
§ 371 (c)(1),
(2) Date: Aug. 23, 2017

(87) PCT Pub. No.: WO2016/134994
PCT Pub. Date: Sep. 1, 2016

(65) Prior Publication Data
US 2018/0049957 A1    Feb. 22, 2018

(30) Foreign Application Priority Data
Feb. 25, 2015   (EP) ..................... 15156452

(51) Int. Cl.
| A61K 8/11 | (2006.01) |
| A61Q 13/00 | (2006.01) |
| A61K 8/04 | (2006.01) |
| A61K 8/73 | (2006.01) |
| C11D 3/50 | (2006.01) |
| C11D 3/22 | (2006.01) |
| C11D 17/00 | (2006.01) |
| C11D 17/06 | (2006.01) |

(52) U.S. Cl.
CPC ............... *A61K 8/11* (2013.01); *A61K 8/044* (2013.01); *A61K 8/737* (2013.01); *A61Q 13/00* (2013.01); *C11D 3/225* (2013.01); *C11D 3/50* (2013.01); *C11D 3/505* (2013.01); *C11D 17/0017* (2013.01); *C11D 17/0039* (2013.01); *C11D 17/06* (2013.01); *A61K 2800/52* (2013.01); *A61K 2800/548* (2013.01); *A61K 2800/5422* (2013.01); *A61K 2800/56* (2013.01)

(58) Field of Classification Search
CPC .......... A23V 2002/00; A23V 2200/332; A23V 2250/21; A61K 2800/412; A61K 2800/56; A61K 8/11; A61K 8/8152; A61K 8/84; A61K 8/922; A23L 27/72; A23L 33/15; A61Q 13/00; A61Q 15/00; A61Q 19/00; A61Q 19/10; A61Q 5/02; A61Q 5/12
See application file for complete search history.

(56) References Cited

U.S. PATENT DOCUMENTS

| 4,428,869 A | 1/1984 | Munteanu et al. |
| 7,968,510 B2 * | 6/2011 | Smets .................. A61K 8/8152 428/402.2 |
| 2008/0118568 A1 | 5/2008 | Smets et al. |
| 2011/0269658 A1 * | 11/2011 | Dihora ..................... A61K 8/11 510/119 |

FOREIGN PATENT DOCUMENTS

| EP | 1 588 760 A1 | 10/2005 |
| WO | 95/16432 A2 | 6/1995 |
| WO | 2006/018694 A1 | 2/2006 |
| WO | 2013/026657 A1 | 2/2013 |
| WO | 2014/064255 A2 | 5/2014 |

OTHER PUBLICATIONS

"Biesterfeld Lieferprogramm Cosmetic, Hydroxypropyl Guar," Aug. 2009, pp. 1-11.

* cited by examiner

*Primary Examiner* — Audrea B Coniglio
*Assistant Examiner* — Audrea Buckley
(74) *Attorney, Agent, or Firm* — Dilworth & Barrese, LLP

(57) ABSTRACT

The invention relates to stable dispersions, containing (a) 50 to 80% by weight of perfume oils, (b) 10 to 30% by weight of encapsulated fragrances, (c) 0.01 to 0.1% by weight of non-ionic polymers of the type of hydrophobically modified hydroxylalkyl guar compounds, with the proviso that the constituents together with water and optionally other typical auxiliary agents and additives add up to 100% by weight.

9 Claims, No Drawings

STABLE DISPERSIONS

FIELD OF THE INVENTION

The invention concerns the field of cosmetic and detergent preparations and concerns new fragrance dispersions with a high content of perfume oils and encapsulated fragrances that are characterized by particularly high stability.

PRIOR ART

The use of perfume oils in detergents and cleaning agents makes it possible for the user to experience a fragrance, but this fragrance quickly dissipates after completion of the washing process and drying of the textiles. In order to provide textiles during the washing process with a fragrance experience that lasts over a relatively long period, i.e. also during wear, fragrances in encapsulated form are added to the formulations. The capsules are configured such that they are resistant under wash conditions and release the fragrances, optionally in a delayed-release manner, only under mechanical stress such as friction.

However, problems arise in the production of ready-made products that contain combinations of perfume oils and capsule slurries (capsules suspended in water). The production of the products is already complex, as the perfume oils and the capsules must be added separately. It would be advantageous if they could be added in a single step. However, a mixture of perfume oil and an aqueous capsule slurry is not stable and separates immediately into water, an oil phase, and capsules. In this case, the use of dispersants or emulsifiers is also only possible to a limited extent, and many capsules release their ingredients (e.g. fragrances) in a surfactant environment.

Numerous possibilities for stabilizing emulsions and dispersions are known from the prior art.

For example, WO 1995 016432 A2 (P&G) from the year 1995 describes cosmetic cleaning agents for topical application to the skin that comprise a surfactant, a cosmetic or a pharmaceutical active ingredient for the hair or skin, and an aqueous carrier. In example II, (pp. 45-46), a cleaning/care shampoo is disclosed as a cleaning agent that contains a perfume component I (ordinary perfume oil) and an encapsulated perfume component II, as well as the nonionic polymer xanthan.

The stabilization of preparations by addition of polysaccharides of the alkylgalacomannan type is known from the documents WO 1999 045893 A1 (HENKEL) and EP 0795321 A1 (L'OREAL); however, no capsules or solid particles are dispersed.

The two documents WO 2006 018694 A1 (FIRMENICH) and DE 102008051799 A1 (HENKEL) describe the suspension of perfumed microcapsules in aqueous solutions with mixtures of nonionic and cationic polymers. However, the capsules contain only very small amounts of fragrances, which are released during storage.

WO 2013 026657 A1 (UNILEVER) describes active substance particles whose outer surface is composed of nonionic polysaccharides, including hydroxypropyl guar, which is disclosed as a capsule wall component.

Core-shell capsules with a capsule wall of polycarboxylic acids are known from WO 2014/064255 A2 (GIVAUDAN). Described is stabilization of the capsules during storage in a medium at a specified pH.

In patent application EP 0987006 A1 (BEIERSDORF), emulsions are described that are stabilized with nanoparticles. However, these are 1000 times smaller than conventional microcapsules, so they show a completely different dispersion behavior.

The subject matter of EP 1588760 A1 (INT FLAVORS & FRAGRANCES INC) concerns skin and hair treatment agents for the controlled release of fragrances. In example V, a skin cream is also described that contains an ordinary perfume mixture B and an encapsulated perfume mixture (from example I), as well as the nonionic polymer xanthan.

U.S. Pat. No. 4,428,869 A (MUNTEANU et. al) discloses hydroalcoholic compositions for cosmetic purposes, which e.g. are diluted with aqueous ethanol into a perfume (cologne). In examples III, IV and V, mixtures are described that are in the form of a thixotropic fragrant paste and contain the liquid perfume composition A, the powdered perfume compositions B/D/E and "Klucel EF"=hydroxyethylcellulose as a thickener. These pastes are suspended in aqueous ethanol in amounts of 2-95%.

US 2008/118568 A1 (SMETS JOHAN et. al.) concerns the encapsulation of active ingredients, more particularly fragrances, for use in various fields such as cleaning agents or cosmetic preparations that contain the nonionic polymer Aculyn 44.

Finally, the subject matter of US 2011/269658 A1 (DIHORA JITEN ODHAVJI et. al.) concerns encapsulated active ingredients. Example 27 describes shampoos (I-III, VII-VIII), which contain both free and encapsulated fragrances and a salt of the compound hydroxypropyl guar. The latter serves as a stabilizer for the shampoo formulation.

The complex object of the present invention was to provide dispersions that contain up to 80% by weight of fragrances and at most 40% by weight of water, have a content of 10 to 30% by weight of encapsulated fragrances, and are characterized by outstanding storage stability with respect to separation into various phases for at least 6 weeks in the low, medium, and high temperature range. A further performance criterion was that the capsules show sufficient stability in the dispersion of oil, water, capsules and dispersants, i.e. do not release their ingredients in large amounts before they are incorporated into the cosmetic or detergent formulations. The previous addition of dispersants should also not affect the capsules in such a way that they subsequently release their ingredients into the cosmetic and detergent formulations more quickly than they would without said addition of dispersants or emulsifiers.

DESCRIPTION OF THE INVENTION

Subject matter of the invention are stable dispersions, containing
(a) 50 to 80% by weight of perfume oils,
(b) 10 to 30% by weight of encapsulated fragrances, and
(c) 0.01 to 0.1% by weight of nonionic polymers of the type of the hydrophobically modified hydroxyalkyl guar compounds,
with the proviso that the components add up to 100% weight together with water and optionally further typical auxiliaries and additives.

Surprisingly, it was found that up to 30% by weight of microencapsulated fragrances can also be incorporated into aqueous dispersions having a high content of perfume oil by adding to said dispersions only very small amounts of nonionic polymers, especially hydrophobically modified hydroxyalkyl guar compounds. The dispersions are storage-stable for at least 4 weeks at 5, 20 and 40° C. with respect to phase separation and also show satisfactory stability for at least 4 further weeks. Moreover, the capsules do not release any ingredients, more particularly fragrances, in the aqueous dispersion with hydrophobically modified hydroxyalkyl guar compounds. It is particularly advantageous in this context that the stabilizing action is largely independent of the capsule material. However, capsules with walls of melamine-formaldehyde resins or polyurethane are particularly advantageous, as they have also been found to be particularly stable in an aqueous environment. The capsule dispersions obtained in this manner can be incorporated problem-free into cosmetic and detergent formulations.

Perfume Oils

As a rule, the perfume oils suitable as component (a) are natural fragrance mixtures such as those available from plant sources as essential oils. They are selected for example from the group composed of angelica root oil, aniseed oil, arnica blossom oil, basil oil, bay oil, champaca flower oil, silver fir oil, silver fir cone oil, elemi oil, eucalyptus oil, fennel oil, pine needle oil, galbanum oil, geranium oil, gingergrass oil, guaiac wood oil, gurjan balsam oil, helichrysum oil, ho oil, ginger oil, iris oil, cajeput oil, sweet flag oil, camomile oil, camphor oil, cananga oil, cardamom oil, cassia oil, pine needle oil, copaiba balsam oil, coriander oil, spearmint oil, caraway seed oil, cumin oil, lavender oil, lemongrass oil, lime oil, mandarin oil, melissa oil, amber seed oil, myrrh oil, clove oil, neroli oil, niaouli oil, olibanum oil, oregano oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citrus oil, and cypress oil.

Preferred perfume oils include pine oil, citrus oil, jasmine oil, patchouli oil, rose oil, muscatel-sage oil, camellia oil, clove oil, melissa oil, mint oil, cinnamon leaf oil, linden blossom oil, juniper berry oil, vetiver oil, olibanum oil, galbanum oil, labdanum oil, orange blossom oil, neroli oil, orange peel oil, and sandalwood oil.

Fragrances

The fragrances suitable as component (B) are not subject to any restrictions whatsoever. It is therefore possible to use as fragrances individual odorant compounds, either synthetic or natural compounds of the class of esters, ethers, aldehydes, ketones, alcohols, hydrocarbons, acids, carbonic esters, aromatic hydrocarbons, aliphatic hydrocarbons, saturated and/or unsaturated hydrocarbons, and mixtures thereof.

The fragrance aldehydes or fragrance ketones used may be all common fragrance aldehydes and fragrance ketones typically used to produce a pleasant fragrance sensation. Suitable fragrance aldehydes and fragrance ketones are commonly known to the person skilled in the art. The fragrance ketones may comprise all ketones which are able to impart a desired fragrance or a sensation of freshness. Mixtures of different ketones may also be used. For example, the ketone may be selected from the group consisting of Buccoxime, isojasmone, methyl β-naphthyl ketone, musk indanone, Tonalid/musk plus, α-damascone, β-damascone, δ-damascone, isodamascone, damascenone, damarose, methyl dihydrojasmonate, menthone, carvone, camphor, fenchone, α-ionone, β-ionone, dihydro-β-ionone, γ-methyl so-called ionone, fleuramone, dihydrojasmone, cis-jasmone, Iso-E-Super, methyl cedrenyl ketone or methyl cedrylone, acetophenone, methyl acetophenone, para-methoxyacetophenone, methyl β-naphthyl ketone, benzylacetone, benzophenone, para-hydroxyphenylbutanone, celery ketone or Livescone, 6-isopropyldecahydro-2-naphthone, dimethyloctenone, Freskomenthe, 4-(1-ethoxyvinyl)-3,3,5,5-tetramethyl cyclohexanone, methyl heptenone, 2-(2-(4-methyl-3-cyclohexen-1-yl)propyl)cyclopentanone, 1-(p-menthen-6(2)-yl)-1-propanone, 4-(4-hydroxy-3-methoxyphenyl)-2-buta none, 2-acetyl-3,3-dimethyl norbornane, 6,7-dihydro-1,1,2,3,3-pentamethyl-4 (5H)-indanone, 4-damascol, dulcinyl or cassione, gelsone, hexalone, isocyclemone E, methyl cyclocitrone, methyl lavender ketone, orivone, para-tert-butylcyclohexanone, verdone, delphone, muscone, neobutenone, plicatone, veloutone, 2,4,4,7-tetramethyloct-6-en-3-one, tetramerane, hedione and mixtures thereof. The ketones may preferably be selected from α-damascone, δ-damascone, isodamascone, carvone, γ-methyl ionone, Iso-E-Super, 2,4,4,7-tetramethyloct-6-en-3-one, benzyl acetone, β-damascone, damascenone, methyl dihydrojasmonate, methyl cedrylone, hedione and mixtures thereof.

Suitable fragrance aldehydes may be any aldehydes that provide a desired fragrance or feeling of freshness corresponding to the fragrance ketones. However, they can also be individual aldehydes or aldehyde mixtures. Suitable aldehydes are for example melonal, triplal, ligustral, adoxal, anisaldehyde, cymal, ethyl vanillin, florhydral, floralozone, helional, heliotropin, hydroxycitronellal, koavone, laurin aldehyde, canthoxal, lyral, lilial, adoxal, anisaldehyde, cumal methylnonyl acetaldehyde, citronellal, citronellyl oxyacetaldehyde, cyclamene aldehyde, bourgeonal, p,t-bucinal, phenylacetaldehyde, undecylenic aldehyde, vanillin; 2,6,10-trimethyl-9-undecenal, 3-dodecen-1-al, α-n-amylcinnamaldehyde, 4-methoxybenzaldehyde, benzaldehyde, 3-(4-tert-butylphenyl)-propanal, 2-methyl-3-(para-methoxyphenylpropanal), 2-methyl-4-(2,6,6-trimethyl-2(I)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzaldehyde, 1,2,3,4,5,6,7,8-octahydro-8,8-dimethyl-2-naphthaldehyde, 2,4-dimethyl-3-cyclohexene-1-carboxyaldehyde, 2-methyl-3-(isopropyl phenyl)propanal, decyl aldehyde, 2,6-dimethyl-5-heptenal; 4-(tricyclo[5.2.1.0(2, 6)]-decylidene-8)-butanal; octahydro-4,7-methanol H-indene carboxaldehyde; 3-ethoxy-4-hydroxybenzaldehyde, para-ethyl-α,α-dimethylhydrocinnamaldehyde, α-methyl-3, 4-(methylene dioxy)-hydrocinnamaldehyde, 3,4-methylene dioxybenzaldehyde, α-n-hexylcinnamaldehyde, m-cymene-7-carboxaldehyde, α-methyl phenylacetaldehyde, 7-hydroxy-3,7-dimethyl octanal, undecenal, 2,4,6-trimethyl-3-cyclohexene-1-carboxaldehyde, 4-(3)(4-methyl-3-pentenyl)-3-cyclohexene carboxaldehyde, 1-dodecanal, 2,4-dimethylcyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5, 9-undecadienal, 2-methyl-3-(4-tertbutyl)propanal, 3-(4-ethylphenyl)-2,2-dimethylpropanal, 3-(4-methoxyphenyl)-2-methylpropanal, methyl nonylacetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropyl phenyl)-2-methylpropan-1-al, 3-(4-ethylphenyl)-2,2-dimethylpropan-1-al, 3-(4-tert-butylphenyl)-2-methylpropanal, 3-(3,4-methylendioxy-phenyl)-2-methylpropan-1-al, 3-(4-ethylphenyl)-2,2-dimethylpropanal, 3-(3-isopropyl phenyl)-butan-1-al, 2,6-dimethylhept-5-en-1-al, dihydrocinnamaldehyde, 1-methyl-4-(4-methyl-3-pentenyl)-3-cyclohexene-1-carboxaldehyde, 5 or 6 methoxyhexahydro-4,7-methanoindan-1 or 2-carboxyaldehyde, 3,7-dimethyloctan-1-al, 1-undecanal, 10-undecen-1-al, 4-hydroxy-3-methoxybenzaldehyde, 1-methyl- 3-(4-methylpentyl)-3-cyclohexene-carboxyaldehyde, 7-hydroxy-3,7-dimethyloctanal; trans-4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexene carboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindan-1-carboxaldehyde, octanal, 2-methyl octanal, α-methyl-4-(1-methylethyl)benzene acetaldehyde, 6,6-dimethyl-2-norpinene-2-propionaldehyde, paramethyl phenoxyacetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methyl nonyl acetaldehyde, 1-p-menthene-q-carboxaldehyde, citral or mixtures thereof, lilial citral, 1-decanal, n-undecanal, n-dodecanal, florhydral, 2,4-dimethyl-3-cyclohexene-1-carboxaldehyde 4-methoxybenzaldehyde, 3-methoxy-4-hydroxybenzaldehyde, 3-ethoxy-4-hydroxybenzaldehyde, 3,4-methylene dioxybenzaldehyde, and 3,4-dimethoxybenzaldehyde and mixtures thereof. As mentioned in the above examples, the fragrance aldehydes and fragrance ketones can have an aliphatic, cycloaliphatic, aromatic, ethylenically unsaturated structure or a combination of these structures. Moreover, there may also be further heteroatoms or polycyclic structures. The structures can have suitable substituents such as hydroxyl or amino groups. For further suitable fragrances selected from aldehydes and ketones, reference is made to "Steffen Arctander, published 1960 and 1969 respectively, reprinted 2000 ISBN: Flavoring Agent Chemicals Vol. 1: 0-931710-37-5, Flavoring Agent Chemicals Vol. 2: 0-931710-38-3."

Examples of suitable odorant compounds of the ester type include benzyl acetate, phenoxyethyl isobutyrate, p-tert-butylcyclohexyl acetate, linalyl acetate, dimethylbenzyl carbinyl acetate (DMBCA), phenylethyl acetate, benzyl acetate, ethyl methyl phenylglycinate, allyl cyclohexyl propionate, styrallyl propionate, benzyl salicylate, cyclohexyl salicylate, floramat, melusat, and jasmacyclate. Examples of odorant compounds of the hydrocarbon type include terpenes such as limonene and pinene. Examples of suitable fragrance alcohols of the ether type include benzyl ethyl ether and ambroxan. Examples of suitable fragrance alcohols include 10-undecen-1-ol, 2,6-dimethylheptan-2-ol, 2-methyl butanol, 2-methyl pentanol, 2-phenoxyethanol, 2-phenyl propanol, 2-tert-butyl cyclohexanol, 3,5,5-trimethyl cyclohexanol, 3-hexanol, 3-methyl-5-phenyl pentanol, 3-octanol, 1-octen-3-ol, 3-phenyl propanol, 4-heptenol, 4-isopropyl cyclohexanol, 4-tert-butyl cyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, 3-terpineol, butyl salicylate, citronellol, cyclohexyl salicylate, decanol, dihydromyrcenol, dimethylbenzyl carbinol, dimethyl heptanol, dimethyl octanol, ethyl salicylate, ethylvanilin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol, and if a plurality of fragrance alcohols is present, they may be selected independently of one another.

So-called fragrance precursors (prodrugs) are also suitable as fragrances. This class of compounds comprises compounds which release a desired odor molecule and/or fragrance molecule through the breaking of a chemical bond, by hydrolysis, for example. In order to form a fragrance precursor, a desired fragrance raw material is typically joined chemically to a carrier, preferably a carrier of low or moderate volatility. The combination results in a less volatile and more strongly hydrophobic fragrance precursor, with better attachment to materials. The fragrance is released subsequently by breaking of the bond between the fragrance raw material and the carrier, as a result of the change in pH, for example (through perspiration during wear, for example), atmospheric humidity, heat and/or sunlight during storage or drying on a clothesline.

The fragrance raw material for use in fragrance precursors typically comprises saturated or unsaturated volatile compounds containing an alcohol, an aldehyde and/or a ketone group. The fragrance raw materials that are useful herein include any pleasant smelling fragrances or mixtures of substances which have already been described above.

Particularly advantageous fragrance precursors which can be used conform to Formula (III)

R—C(OR$^1$)(OR$^2$)—OR$^3$    (III)

where R denotes hydrogen, linear $C_1$-$C_8$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl and mixtures thereof; $R^1$, $R^2$ and $R^3$ independently are linear, branched, or substituted $C_1$-$C_{20}$ alkyl; linear, branched or substituted $C_2$-$C_{20}$ alkenyl; substituted or unsubstituted cyclic $C_3$-$C_{20}$ alkyl; substituted or substituted $C_6$-$C_{20}$ aryl, substituted or unsubstituted $C_2$-$C_{40}$ alkyleneoxy; substituted or unsubstituted $C_3$-$C_{40}$ alkylene oxyalkyl; substituted or unsubstituted $C_6$-$C_{40}$ alkylene aryl; substituted or unsubstituted $C_6$-$C_{32}$ aryloxy; substituted or unsubstituted $C_6$-$C_{40}$ alkylene oxyaryl; $C_6$-$C_{40}$ oxyalkylenearyl and mixtures thereof.

The use of such substances, in particular in (preferably water-insoluble) microcapsules, corresponds to a preferred embodiment of the invention.

Further particularly preferred fragrance precursors are acetals or ketals, preferably of Formula (IV):

R—C(R$^1$)(OR$^3$)—OR$^2$    (IV)

where R denotes a linear $C_1$-$C_{20}$ alkyl, branched $C_3$-$C_{20}$ acyl, cyclic $C_6$-$C_{20}$ alkyl, branched cyclic $C_6$-$C_{20}$ alkyl, linear $C_2C_{20}$ alkenyl, branched $C_3$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl, and mixtures thereof; $R^1$ is hydrogen or R; $R^2$ and $R^3$, each independently of one another, are selected from the group composed of linear $C_1$-$C_{20}$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, $C_6$-$C_{20}$ aryl, substituted $C_7$-$C_{20}$ aryl, and mixtures thereof. The use of such substances, in particular in (preferably water-insoluble) microcapsules, corresponds to a preferred embodiment of the invention.

Further particularly advantageous fragrance precursors suitable for use conform to Formula (V)

R$^4$O—C(OR$^1$)(OR$^3$)—OR$^2$    (V)

where $R^1$, $R^2$, $R^3$ and $R^4$, independently of one another, are linear, branched or substituted $C_1$-$C_{20}$ alkyl; linear, branched or substituted $C_2$-$C_{20}$ alkenyl; substituted or unsubstituted cyclic $C_5$-$C_{20}$ alkyl; substituted or unsubstituted $C_6$-$C_{20}$ aryl, substituted or unsubstituted $C_2$-$C_{40}$ alkyleneoxy; substituted or unsubstituted $C_3$-$C_{40}$ alkylene oxyalkyl; substituted or unsubstituted $C_6$-$C_{40}$ alkylene aryl; substituted or unsubstituted $C_6$-$C_{32}$ aryloxy; substituted or unsubstituted $C_6$-$C_{40}$ alkylene oxyaryl; $C_6$-$C_{40}$ oxyalkylene aryl; and mixtures thereof. The use of such substances, in particular in (preferably water-insoluble) microcapsules, corresponds to a preferred embodiment of the invention.

It is particularly preferable if the fragrances used comprise silicic acid ester mixtures. Silicic acid esters are described, for example, by Formula (V)

(V)

where each R is independently selected from the group containing H, linear or branched, saturated or unsaturated, substituted or unsubstituted $C_1$-$C_6$ hydrocarbon radicals and fragrance alcohol radicals and/or biocide alcohol radicals, m adopts values from the range of 1 to 20, and n adopts values from the range of 2 to 100. Preferably, the silicic esters of the formulae contain at least one fragrance alcohol radical and/or biocide alcohol radical.

The silicic acid ester mixtures can be used in encapsulated, but also unencapsulated form. The presence of silicic acid ester mixtures often makes it possible to even further improve the fragrance impression obtainable, with respect to both pleasant aroma and intensity. The fragrance impression is not only better from a qualitative standpoint, i.e. with respect to pleasant aroma, but is also longer-lasting.

The silicic acid ester mixtures can also be contained in the microcapsules. If the silicic acid ester mixtures in the microcapsules preferably account for at least 2% by weight of the total amount of encapsulated fragrances, i.e. in % by weight relative to the amount of encapsulated fragrances, this constitutes a preferred embodiment of the invention, which provides a further improvement in the desired fragrance effect after drying.

Particularly suitable fragrance precursors are reaction products of compounds comprising at least one primary and/or secondary amine group, for example an aminofunctional polymer, in particular an aminofunctional silicone, and a fragrance component selected from a ketone, an aldehyde, and mixtures thereof. The use of such substances, in particular in (preferably water-insoluble) microcapsules, corresponds to a preferred embodiment of the [invention].

The total amount of fragrances in the detergents and cleaning agents according to the invention is preferably between 0.01 and 5% by weight, particularly preferably between 0.1 and 3% by weight and most particularly preferably between 0.5 and 2 percent by weight based on the total amount of the agent.

Preferably, mixtures of various fragrances (from the various fragrance classes mentioned above) are used which combine to produce an attractive scent note. In this case, the total amount of the at least one fragrance is the amount of all of the fragrances in the mixture together relative to the total amount of the agent.

Capsules

The fragrances that form component (b) are in the form of capsules. These are understood to be spherical aggregates that contain at least one solid or liquid core surrounded by at least one continuous membrane. The fragrances can be encapsulated by coating materials and be present as macrocapsules with diameters of about 0.1 to about 5 mm or microcapsules with diameters of about 0.0001 to about 0.1 mm.

Coating Materials

Suitable coating materials include starches, for example, including their degradation products and also chemically or physically produced derivatives (especially dextrins and maltodextrins), gelatin, gum arabic, agar-agar, ghatti gum, gellan gum, modified and nonmodified celluloses, pullulan, curdlan, carrageenans, alginic acid, alginates, pectin, inulin, xanthan gum, and mixtures of two or more of these substances.

The solid encapsulating material is preferably a gelatin (more particularly pork, beef, poultry and/or fish gelatin), preferably with a swelling factor of greater than or equal to 20, preferably of greater than or equal to 24. Particularly preferred among these substances is gelatin, since it is readily available and can be acquired with different swelling factors.

Likewise preferred are maltodextrins (especially those based on cereals, specifically corn, wheat, tapioca, or potatoes), preferably with DE values in the range of 10 to 20. Further preferred are celluloses (e.g. cellulose ethers), alginates (e.g. sodium alginate), carrageenan (e.g. beta-, iota-, lambda- and/or kappa-carrageenan), gum arabic, curdlan and/or agar-agar.

Likewise preferred are alginate capsules, such as those described comprehensively in the following specifications: EP 0389700 A1, U.S. Pat. Nos. 4,251,195, 6,214,376, WO 2003 055587 or WO 2004 050069 A1.

In a further preferred embodiment, the shell of the capsules is composed of melamine-formaldehyde resins or coacervation products of cationic monomers or biopolymers (such as chitosan) and/or anionic monomers or polymers such as (meth)acrylic acid or alginic acid or (meth)acrylates or alginates.

Encapsulation Methods

The capsules are generally finely dispersed liquid or solid phases coated with film-forming polymers, in the production of which the polymers are deposited onto the material to be encapsulated after emulsification and coacervation or interfacial polymerization. According to another process, molten waxes are absorbed in a matrix ("microsponge") which, as microparticles, may be additionally coated with film-forming polymers. According to a third method, particles are coated with alternating layers of differently charged polyelectrolytes ("layer-by-layer" method). The microscopically small capsules can be dried in the same way as powders. In addition to single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides such as starch or dextran, polypeptides, protein hydrolysates, sucrose and waxes. Examples of semisynthetic membrane materials are chemically modified celluloses, particularly cellulose esters and ethers, such as cellulose acetate, ethyl cellulose, hydroxypropyl cellulose, hydroxypropyl methyl cellulose and carboxymethyl cellulose, and starch derivatives, particularly starch ethers and esters. Synthetic membrane materials are, for example, polymers, such as polyacrylates, polyamides, polyvinyl alcohol or polyvinyl pyrrolidone.

Examples of microcapsules known from the prior art are the following commercial products (the membrane material is shown in brackets) Hallcrest Microcapsules (gelatin, gum arabic), Coletica Thalaspheres (maritime collagen), Lipotec Millicapsules (alginic acid, agar agar), Induchem Unispheres (lactose, microcrystalline cellulose, hydroxypropylmethyl cellulose), Unicerin C30 (lactose, microcrystalline cellulose, hydroxypropylmethyl cellulose), Kobo Glycospheres (modified starch, fatty acid esters, phospholipids), Softspheres (modified agar agar), Kuhs Probiol Nanospheres (phospholipids), as well as Primaspheres and Primasponges (chitosan, alginates) and Primasys (phospholipids).

Chitosan microcapsules and processes for their production are sufficiently known from the prior art [WO 01/01926, WO 01/01927, WO 01/01928, WO 01/01929]. Microcapsules having average diameters in the range of 0.0001 to 5, preferably 0.001 to 0.5 and more particularly 0.005 to 0.1 mm, consisting of an envelope membrane and a matrix comprising the active substances, may be obtained, for example, by
(a) preparing a matrix from gel formers, cationic polymers and active substances,
(b) optionally dispersing the matrix in an oil phase, and
(c) treating the dispersed matrix with aqueous solutions of anionic polymers, and optionally removing the oil phase.

Steps (a) and (c) here are interchangeable provided that anionic polymers are used in step (a) instead of the cationic polymers, and vice versa.

The capsules can also be produced by alternately enveloping the active substance with layers of differently charged polyelectrolytes (layer-by-layer technology). In this context, reference is made to European patent EP 1064088 B1 (Max-Planck Gesellschaft).

Nonionic Polymers

The nonionic polymers comprising component (c) are polysaccharides, especially hydrophobically modified hydroxyalkyl guar compounds. Particularly preferred are thickeners of the type $C_{8}$-$C_{22}$ hydroxyalkyl hydroxypropyl guar, and more particularly $C_{18}$-$C_{22}$ hydroxyalkyl hydroxypropyl guar. Corresponding products are commercially available under the trade name ESAFLOR HM22 (Lamberti Spa).

Method

A further subject matter of the invention concerns a method for the stabilization of aqueous dispersions containing perfume oils and encapsulated fragrances, in which one adds to said dispersions 0.01 to 0.1% by weight of nonionic polymers, especially polysaccharides and more particularly polymers of the type of hydrophobically modified hydroxyalkyl guar compounds. The dispersions stabilized in this manner are characterized in that they contain about 50 to about 80% by weight, preferably about 60 to about 70% by weight of perfume oils and about 10 to about 30% by weight, preferably about 15 to about 20% by weight of encapsulated fragrances, with the proviso that these indicated amounts, together with nonionic polymers, water and optionally further common auxiliaries and additives, add up to 100% by weight. A further characteristic of the dispersions is that they are in triphasic form.

Industrial Applicability

A further subject matter of the invention concerns cosmetic preparations on the one hand and washing, rinsing, and cleaning agents on the other that contain the dispersions according to the invention, for example in amounts of about 0.1 to about 5% by weight and more particularly about 0.5 to about 2% by weight.

WSR Agents

Washing, rinsing, and cleaning agents (abbreviated as WRC agents) within the meaning of the present invention may be present in solid form as powders, granulates, tablets and the like, but also in liquid, gel, or paste form. These are preferably washing agents suitable for both machine and manually-washed laundry, more particularly textiles. These may be detergents or cleaning agents for industrial use or for household use. For example, cleaning agents may also be used for the cleaning of hard surfaces. For example, these may be dishwashing agents that are used for machine or manual dishwashing. They may also be common industrial or household cleaners, with which hard surfaces such as furniture surfaces, slabs, tiles, and wall and floor coverings are cleaned. In addition to dishes, suitable examples include all other common hard surfaces, more particularly composed of glass, ceramic, plastic, or metal, in household and industrial use.

The WRC agents may also contain other common commercial components, such as surfactants, builders, bleaching agents, bleaching agent activators, thickeners, enzymes, electrolytes, pH adjusting agents, dyes and fragrances, foam inhibitors, anti-redeposition agents, optical brighteners, graying inhibitors, anti-wrinkle agents, antimicrobial active ingredients, preservatives, antioxidants, antistatics, UV adsorbers, heavy metal complexing agents and the like. These auxiliaries are described in further detail below:

Surfactants

In addition to the nonionic surfactants, anionic, cationic, amphoteric and/or nonionic surfactants and branched alkyl sulfates can also be used as surfactants for the production of the detergents or cleaning agents.

Preferred nonionic surfactants are alkoxylated, advantageously ethoxylated, particularly primary alcohols preferably containing 8 to 18 carbon atoms and, on average, 1 to 12 moles of ethylene oxide (EO) per mole of alcohol, in which the alcohol radical may be linear or, preferably, methyl-branched in the 2-position or may comprise linear and methyl-branched groups in the mixture typically present in oxoalcohol radicals. Particularly preferred are, however, alcohol ethoxylates with linear radicals from alcohols of natural origin with 12 to 18 carbon atoms, e.g. from coco-, palm-, tallow- or oleyl alcohol, and an average of 2 to 8 EO per mole of alcohol. Examples of preferred ethoxylated alcohols include $C_{12-14}$-alcohols with 3 EO, 4 EO, or 7 EO, $C_{9-11}$-alcohols with 7 EO, $C_{13-15}$-alcohols with 3 EO, 5 EO, 7 EO or 8 EO, $C_{12-18}$-alcohols with 3 EO, 5 EO or 7 EO and mixtures thereof, such as mixtures of $C_{12-14}$-alcohols with 3 EO and $C_{12-18}$-alcohols with 5 EO. The cited degrees of ethoxylation constitute statistical average values that can be a whole or a fractional number for a specific product. Preferred alcohol ethoxylates have a narrowed homolog distribution (narrow range ethoxylates, NRE). In addition to these nonionic surfactants, fatty alcohols with more than 12 EO can also be used. Examples of these are tallow fatty alcohol with 14 EO, 25 EO, 30 EO or 40 EO. Nonionic surfactants that contain EO and PO groups together in the molecule may also be used according to the invention. Block copolymers having EO-PO block units or PO-EO block units, but also EO-PO-EO copolymers or PO-EO-PO copolymers, can be used in this context. Also usable, of course, are mixed alkoxylated nonionic surfactants in which EO and PO units are distributed statistically rather than in block fashion. Such products are obtainable by the simultaneous action of ethylene oxide and propylene oxide on fatty alcohols.

A further class of nonionic surfactants that can be advantageously used for the production of detergents or cleaning agents are the alkylpolyglycosides (APG). Useable alkypolyglycosides satisfy the general formula RO(G)Z, in which R stands for a linear or branched, more particularly methyl-branched at the 2 position, saturated or unsaturated, aliphatic radical with 8 to 22, preferably 12 to 18 C atoms and G is the symbol for a glycose unit with 5 or 6 C atoms, preferably glucose. The degree of glycosylation z is between 1.0 and 4.0, preferably between 1.0 and 2.0 and more particularly between 1.1 and 1.4.

Nonionic surfactants of the amine oxide type, e.g., N-cocoalkyl-N,N-dimethylamine oxide and N-tallow alkyl-N,N-dihydroxyethylamine oxide and fatty acid alkanolamides may also be suitable for producing the detergent or cleaning agent. The amount of these nonionic surfactants is preferably no more than that of the ethoxylated fatty alcohols, in particular no more than half thereof.

Other suitable surfactants are polyhydroxy fatty acid amides of the formula

R—CO—N($R^1$)—[Z], in which RCO stands for an aliphatic acyl group with 6 to 22 carbon atoms, R1 for hydrogen, an alkyl or hydroxyalkyl group with 1 to 4 carbon atoms and [Z] for a linear or branched polyhydroxyalkyl group with 3 to 10 carbon atoms and 3 to 10 hydroxyl groups. The polyhydroxyfatty acid amides are known substances that can ordinarily be obtained by reductive amination of a reducing sugar with ammonia, an alkylamine or an alkanolamine and subsequent acylation with a fatty acid, a fatty acid alkyl ester or a fatty acid chloride. The group of polyhydroxyfatty acid amides also includes compounds of the formula R—CO—N(R1-O—R2)-[Z], in which R is a linear or branched alkyl or alkenyl radical containing 7 to 12 carbon atoms, R1 is a linear, branched or cyclic alkyl radical or an aryl radical containing 2 to 8 carbon atoms and R2 is a linear, branched or cyclic alkyl radical or an aryl radical or an oxyalkyl radical containing 1 to 8 carbon atoms, with $C_{1-4}$ alkyl or phenyl radicals being preferred, and [Z] is a linear polyhydroxyalkyl radical, of which the alkyl chain is substituted by at least two hydroxy radicals, or alkoxylated, preferably ethoxylated or propoxylated derivatives of that radical. [Z] is preferably obtained by reductive amination of a reduced sugar, for example, glucose, fructose, maltose, lactose, galactose, mannose or xylose. The N-alkoxy- or N-aryloxy-substituted compounds may then be converted in the required polyhydroxyfatty acid amides by reaction with fatty acid methyl esters in the presence of an alkoxide as a catalyst.

The preferred content of nonionic surfactants in the liquid detergents and cleaning agents is 5 to 30% by weight, more preferably 7 to 20% by weight and most particularly 9 to 15% by weight, in each case relative to the entire content of the agent.

Examples of suitable anionic surfactants are those of the sulfonate and sulfate type. Suitable surfactants of the sulfonate type are preferably $C_{9-3}$-alkylbenzene sulfonates, olefin sulfonates, i.e. mixtures of alkene- and hydroxyalkane sulfonates, and disulfonates, as are obtained, for example, from $C_{12-18}$-monoolefins having a terminal or internal double bond, by sulfonation with gaseous sulfur trioxide and subsequent alkaline or acidic hydrolysis of the sulfonation products. Alkane sulfonates obtained from $C_{12-8}$ alkanes by sulfochlorination or sulfoxidation, for example, with subsequent hydrolysis or neutralization, are also suitable. The esters of α-sulfofatty acids (ester sulfonates), e.g. the α-sulfonated methyl esters of hydrogenated coco, palm nut or tallow acids, are also suitable.

Also suitable are sulfonation products of unsaturated fatty acids, for example, oleic acid, in small amounts, preferably in amounts of no more than about 2 to 3% by weight. Preferred in particular are α-sulfofatty acid alkyl esters having an alkyl chain with no more than 4 C atoms in the ester group, for example methyl ester, ethyl ester, propyl ester, and butyl ester. The methyl esters of α-sulfofatty acids (MES), but the saponified disalts thereof as well, are used particularly advantageously.

Fatty acid derivatives of amino acids, for example, of N-methyltaurine (taurides) and/or of N-methylglycine (sarcosides) may be considered as further anionic surfactants. The sarcosides or sarcosinates are particularly preferred in this case and here most especially sarcosinates of higher and optionally mono- or polyunsaturated fatty acids such as oleyl sarcosinate.

Further suitable anionic surfactants are sulfonated fatty acid glycerol esters. Fatty acid glycerol esters are understood to refer to mono-, di- and triesters and mixtures thereof obtained during production of a monoglycerol with 1 to 3 mol of fatty acid by esterification, or upon transesterification of triglycerides with 0.3 to 2 mol of glycerol. Preferred sulfonated fatty acid glycerol esters are the sulfonation products of saturated fatty acids having 6 to 22 carbon atoms, for example, caproic acid, caprylic acid, capric acid, myristic acid, lauric acid, palmitic acid, stearic acid, or behenic acid.

Preferred alk(en)yl sulfates are the alkali, and in particular sodium, salts of sulfuric acid semi-esters of $C_{12}$-$C_{18}$ fatty alcohols, for example from coconut fatty alcohol, tallow fatty alcohol, lauryl, myristyl, cetyl, or stearyl alcohol, or of the $C_{10}$-$C_{20}$ oxo-alcohols, and those semi-esters of secondary alcohols of those chain lengths. Additionally preferred are alk(en)yl sulfates of the aforementioned chain length that contain a synthetic straight-chain alkyl residue produced on a petrochemical basis, which possess a breakdown behavior analogous to those appropriate compounds based on fat-chemistry raw materials. For purposes of washing technology, the $C_{12}$-$C_{16}$ alkyl sulfates and $C_{12}$-$C_{15}$ alkyl sulfates, as well as $C_{14}$-$C_{15}$ alkyl sulfates, are preferred. 2,3-Alkyl sulfates that can be obtained, for example, as commercial products of the Shell Oil Company under the trade name DAN®, are also suitable anionic surfactants.

The sulfuric acid monoesters of straight-chain or branched $C_{7-21}$ alcohols ethoxylated with 1 to 6 mol of ethylene oxide, such as 2-methyl-branched $C_{9-11}$ alcohols having an average of 3.5 mol of ethylene oxide (EO) units or $C_{12-18}$ fatty alcohols having 1 to 4 EO units are also suitable. Because of their high foaming behavior, they are used in cleaning agents only in relatively small amounts, for example in amounts of 1 to 5% by weight.

Other suitable anionic surfactants include the salts of alkylsulfosuccinic acid, also referred to as sulfosuccinates or sulfosuccinic acid esters, and represent the monoesters and/or diesters of sulfosuccinic acid with alcohols, preferably fatty alcohols, and most preferably ethoxylated fatty alcohols. Preferred sulfosuccinates contain $C_{8-18}$ fatty alcohol residues or mixtures thereof. Particularly preferred sulfosuccinates contain a fatty alcohol residue derived from ethoxylated fatty alcohols that, considered per se, represent nonionic surfactants (see description below). Sulfosuccinates whose fatty alcohol residues derive from ethoxylated fatty alcohols having a restricted homolog distribution are particularly preferred. It is likewise also possible to use alk(en)ylsuccinic acid preferably having 8 to 18 carbon atoms in the alk(en)yl chain or salts thereof.

Particularly preferred anionic surfactants are soaps. Saturated and unsaturated fatty acid soaps, such as salts of lauric acid, myristic acid, palmitic acid, stearic acid, (hydrogenated) erucic acid, and behenic acid, are suitable as are more particularly soap mixtures derived from natural fatty acids, e.g., coconut, palm-kernel, olive-oil, or tallow fatty acids.

The anionic surfactants including soaps can be present in the form of their sodium, potassium, or ammonium salts as soluble salts of organic bases, such as mono-, di or triethanolamine. Preferably, the anionic surfactants are in the form of their sodium or potassium salts, more particularly in the form of their sodium salts.

The anionic surfactant content of preferred liquid detergents and cleaning agents is 1 to 30% by weight, preferably 4 to 25% by weight and more particularly 5 to 22% by weight, relative in each case to the entire amount of the agent. Particularly preferably, the amount of fatty acid soap is at least 2% by weight, more preferably at least 3% by weight and even more particularly preferably at least 4% by weight.

So-called gemini surfactants may be considered as additional surfactants for producing the detergents or cleaning agents according to the invention. These include in general compounds having two hydrophilic groups and two hydrophobic groups per molecule. These groups are usually separated from one another by a so-called spacer. This spacer is usually a carbon chain, which should be long enough so that the hydrophilic groups have sufficient spacing to be able to act independently of one another. Such surfactants are characterized in general by an unusually low critical micelle concentration and the ability to greatly reduce the surface tension of water. In exceptional cases, however, the term gemini surfactants is understood to refer not only to dimeric surfactants but also trimeric surfactants.

Suitable gemini surfactants for the production of detergents and cleaning agents include, for example, sulfated hydroxy mixed ethers according to German Patent Application DE-A-4321022 or dimeric alcohol bis-sulfates and trimeric alcohol tris-sulfates and ether sulfates according to German Patent Application DE-A-19503061. End group-capped dimeric and trimeric mixed ethers according to German Patent Application DE-A-19513391 are characterized by their bifunctionality and multifunctionality in particular. The aforementioned end group-capped surfactants have good wetting properties and are low foaming, so they are suitable in particular for use in machine washing or cleaning methods.

Mixtures of anionic and nonionic surfactants are preferred in terms of application engineering. The total surfactant content of the liquid detergents and cleaning agents is preferably less than 40% by weight and particularly preferably less than 35% by weight relative to the total content of the liquid detergents and cleaning agents.

Builders

Phosphates, silicates, aluminum silicates (in particular zeolites), carbonates, organic co-builders, phosphates salts of organic di- and polycarboxylic acids, and mixtures of these substances, may be mentioned in particular as structural materials or builders that can be contained in the liquid detergents and cleaning agents.

Preferred crystalline, layered sodium silicates have the general formula $NaMSi_xO_{2x+1}*H_2O$, where M is sodium or hydrogen, x is a number from 1.9 to 4 and y is a number from 0 to 20, preferred values for x being 2, 3 or 4. Preferred crystalline layered silicates of the given formula are those in which M stands for sodium and x assumes the values 2 or 3. Both β- and δ-sodium disilicates $Na_2Si_2O_5*yH_2O$ are preferred.

Amorphous sodium silicates with a modulus $Na_2O:SiO_2$ ratio of 1:2 to 1:3.3, preferably 1:2 to 1:2.8 and more preferably 1:2 to 1:2.6, which are dissolution-delayed and exhibit secondary wash cycle properties, are also usable. The delay in dissolution compared with conventional amorphous sodium silicates can have been obtained in various ways, for example, by surface treatment, compounding, compressing/compacting or by over-drying. In the context of the present invention, the term "amorphous" is also understood to mean "X-ray amorphous". In other words, the silicates do not produce any of the sharp X-ray reflexes typical of crystalline substances in X-ray diffraction experiments, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This is to be interpreted to mean that the products have microcrystalline regions between 10 and a few hundred nm in size, with values of up to at most 50 nm and especially up to at most 20 nm being preferred. This type of so-called X-ray amorphous silicates similarly possess a delayed dissolution in comparison with conventional water glasses. Compacted/densified amorphous silicates, compounded amorphous silicates and over-dried X-ray-amorphous silicates are particularly preferred.

A suitable fine crystalline, synthetic zeolite containing bound water is preferably zeolite A and/or P. Zeolite MAP™ (commercial product of the Crosfield company), is particularly preferred as the zeolite P. However, zeolite X and mixtures of A, X and/or P are also suitable. Commercially available and preferred in the context of the present invention is, for example, also a co-crystallizate of zeolite X and zeolite A (approx. 80% by weight of zeolite X), which is marketed by SASOL under the brand name VEGOBOND AX® and which can be described by the formula

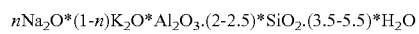

$nNa_2O*(1-n)K_2O*Al_2O_3.(2-2.5)*SiO_2.(3.5-5.5)*H_2O$

The zeolite can be used as a spray-dried powder or also as a non-dried, still moist from its manufacture, stabilized suspension. In the event the zeolite is used as a suspension, it can contain small additions of nonionic surfactants as stabilizers, for example 1 to 3% by weight, relative to the zeolite, of ethoxylated $C_{12}$-$C_{18}$ fatty alcohols having 2 to 5 ethylene oxide groups, $C_{12}$-$C_{14}$ fatty alcohols having 4 to 5 ethylene oxide groups, or ethoxylated isotridecanols. Suitable zeolites exhibit an average particle size of less than 10 μm (volume distribution; measurement method: Coulter counter), and preferably contain 18 to 22% by weight, in particular 20 to 22% by weight, of bound water.

The use of the generally known phosphates as builder substances is also possible, of course, provided such use should not be avoided for environmental reasons. The sodium salts of the orthophosphates, of the pyrophosphates, and in particular of the tripolyphosphates are particularly suitable.

Suitable builders are organic co-builders, more particularly polycarboxylates/polycarboxylic acids, polymeric polycarboxylates, aspartic acid, polyacetals, dextrins and phosphonates.

Examples of polymeric polycarboxylates are the alkali metal salts of the polyacrylic acids or polymethacrylic acids, for example those with a relative molecular weight of 500 to 70,000 g/mol. Within the meaning of the present document, the molecular weights given for polymeric polycarboxylates are weight-average molecular weights $M_w$ of the respective acid form, which were generally determined by gel permeation chromatography (GPC) using a UV detector. The measurement was performed against an external polyacrylic acid standard, which yields realistic molecular weight values because of its structural relationship to the polymers investigated. These data deviate significantly from the molecular weight data in which polystyrene sulfonic acids are used as the standard. The molecular weights measured against polystyrene sulfonic acids are usually much higher than the molecular weights given in the present document.

Suitable polymers include in particular polyacrylates, which preferably have a molecular weight of 2,000 g/mol to 20,000 g/mol. Because of their superior solubility, the short-chain polyacrylates having molecular weights of 2,000 g/mol to 10,000 g/mol and especially preferably from 3,000 g/mol to 5,000 g/mol may in turn be preferred from this group.

Copolymeric polycarboxylates, in particular those of acrylic acid with methacrylic acid and of acrylic acid or methacrylic acid with maleic acid, are also suitable. Copolymers of acrylic acid with maleic acid that contain 50 to 90% by weight of acrylic acid and 50 to 10% by weight of maleic acid have proven particularly suitable. Their relative molecular weight, relative to free acids, is generally 2000 to 70,000 g/mol, preferably 20,000 to 50,000 g/mol, and in particular 30,000 to 40,000 g/mol.

Also especially preferred are biodegradable polymers of more than two different monomer units, e.g., those that contain salts of acrylic acid and maleic acid as well as vinyl alcohol and/or vinyl alcohol derivatives as monomers or containing monomeric salts of acrylic acid and 2-alkylallyl-sulfonic acid as well as sugar derivatives.

Other preferred copolymers are those that preferably have acrolein and acrylic acid/acrylic acid salts and/or acrolein and vinyl acetate as monomers.

Also to be mentioned as further preferred builder substances are polymeric aminodicarboxylic acids, their salts, or their precursor substances. Particularly preferred are polyaspartic acids or their salts and derivatives, which have not only co-builder properties but also a bleach-stabilizing action.

Additional suitable builder substances include polyacetals, which can be obtained by reaction of dialdehydes of polyol carboxylic acids having 5 to 7 carbon atoms and at least three hydroxyl groups. Preferred polyacetals are obtained from dialdehydes such as glyoxal, glutaraldehyde, terephthalaldehyde and mixtures thereof and from polyol carboxylic acids such as gluconic acid and/or glucoheptonic acid.

Other suitable organic builder substances include dextrins, e.g., oligomers and/or polymers of carbohydrates that can be obtained by partial hydrolysis of starches. The hydrolysis may be performed according to conventional methods, e.g., acid catalyzed or enzyme catalyzed methods. These are preferably hydrolysis products having average molecular weights in the range of 400 g/mol to 500,000 g/mol. A polysaccharide with one dextrose equivalent (DE) in the range of 0.5 to 40, in particular from 2 to 30 is preferred, where DE is a conventional measure for the reducing effect of a polysaccharide in comparison with dextrose, which has a DE of 100. Both maltodextrins with a DE between 3 and 20 and dry glucose syrups with a DE between 20 and 37 as well as so-called yellow dextrins and white dextrins with higher molecular weights in the range of 2,000 g/mol to 30,000 g/mol can also be used.

The oxidized derivatives of such dextrins are their reaction products with oxidizing agents that are capable of oxidizing at least one alcohol functional group of the saccharide ring to the carboxylic acid functional group. A product oxidized on $C_6$ of the saccharide ring may be especially advantageous.

A preferred dextrin is described in the British Patent Application GB 9,419,091 B1. The oxidized derivatives of such dextrins are their reaction products with oxidizing agents that are capable of oxidizing at least one alcohol functional group of the saccharide ring to the carboxylic acid functional group. Such oxidized dextrins and methods of synthesizing same are known from the European Patent Applications EP 032202 A, EP 0427349 A, EP 0472042 A and EP 0542496 A and the International Patent Applications WO 1992/018542 A, WO 1993/008251 A, WO 1994/028030 A, WO 1995/007303 A, WO 1995/012619 A and WO 1995/020608 A, for example. A product oxidized on $C_6$ of the saccharide ring may be especially advantageous.

Oxydisuccinates and other derivatives of disuccinates, preferably ethylenediaminedisuccinate, are additional suitable cobuilders. Ethylene-diamine-N,N'-disuccinate (EDDS) is preferably used in the form of its sodium or magnesium salts. In this context, glycerol disuccinates and glycerol trisuccinates as described in the U.S. Pat. Nos. 4,524,009, 4,639,325, European Patent Application EP-A-0150 930 A and Japanese Patent Application JP-A-93/339 896 A, for example, are also preferred.

Further usable organic co-builders are, for example, acetylated hydroxycarboxylic acids and their salts, which can optionally also be present in lactone form and which contain at least 4 carbon atoms and at least one hydroxy group, as well as a maximum of two acid groups. Such co-builders are described, for example, in International Patent Application WO 1995/020029 A.

A further substance class having co-builder properties is represented by the phosphonates. These are, in particular, hydroxyalkane or aminoalkanephosphonates. Among the hydroxyalkanephosphonates, 1-hydroxyethane-1,1-diphosphonate (HEDP) is particularly important as a co-builder. It is preferably used as the sodium salt, in which context the disodium salt reacts neutrally and the tetrasodium salt in alkaline fashion (pH 9). Suitable aminoalkanephosphonates are preferably ethylenediamine tetramethylenephosphonate (EDTMP), diethylenetriamine pentamethylenephosphonate (DTPMP), and their higher homologs. They are preferably used in the form of the neutrally reacting sodium salts, e.g., as the hexasodium salt of EDTMP or as the hepta- and octasodium salt of DTPMP. Of the class of phosphonates, HEDP is preferably used as a builder. The aminoalkanephosphonates furthermore possess a pronounced heavy-metal binding capability. It may accordingly be preferred, especially when the detergents and cleaning agents also contain bleaches, to use aminoalkanephosphonates, in particular DTPMP, or mixtures of the aforementioned phosphonates to produce said agents.

Moreover, all compounds that are capable of forming complexes with alkaline earth ions may be used as co-builders.

Further usable organic builder substances are polycarboxylic acids that may be used in the form of their sodium salts, where polycarboxylic acids are understood to be carboxylic acids having more than one acid functional group. Examples include citric acid, adipic acid, succinic acid, glutaric acid, malic acid, tartaric acid, maleic acid, fumaric acid, saccharic acids, aminocarboxylic acids, nitrilotriacetic acid (NTA), provided that the use thereof is unobjectionable for environmental reasons, and mixtures thereof. Preferred salts include the salts of polycarboxylic acids such as citric acid, adipic acid, succinic acid, glutaric acid, tartaric acid, saccharic acids and mixtures thereof.

The acids per se can also be used. In addition to their builder action, the acids also typically have the property of an acidifying component and therefore also serve to establish a relatively low and mild pH in detergents and/or cleaning agents. More particularly, citric acid, succinic acid, glutaric acid, adipic acid, gluconic acid and any mixtures thereof are to be mentioned in this regard.

Bleaching Agents and Bleaching Catalysts

Among the compounds serving as bleaching agents that yield $H_2O_2$ in water, sodium percarbonate is of particular importance. Additional usable bleaching agents are, for example, sodium perborate tetrahydrate and sodium perborate monohydrate, peroxypyrophosphates, citrate perhydrates, and peracid salts or peracids that yield $H_2O_2$, such as perbenzoates, peroxyphthalates, diperazelaic acid, phthaloimino peracid, or diperdodecanedioic acid. In order to achieve an improved bleaching action when washing at temperatures of 60° C. and below, bleach activators can be incorporated into the detergents and cleaning agents. Compounds which, under perhydrolysis conditions, yield aliphatic peroxycarboxylic acids having preferably 1 to 10 carbon atoms, more particularly 2 to 4 carbon atoms, and/or optionally substituted perbenzoic acid, can be used as bleach activators. Substances that carry O- and/or N-acyl groups having the aforementioned number of carbon atoms, and/or optionally substituted benzoyl groups, are suitable. Polyacylated alkylenediamines, more particularly tetraacetyl ethylenediamine (TAED), acylated triazine derivatives, more particularly 1,5-diacetyl-2,4-dioxyhexahydro-1,3,5-triazine (DADHT), acylated glycolurils, more particularly tetraacetyl glycoluril (TAGU), N-acylimides, more particularly N-nonanoyl succinimide (NOSI), acylated phenol sulfonates, more particularly n-nonanoyl or isononanoyl oxybenzene sulfonate (n- and iso-NOBS), carboxylic acid anhydrides, more particularly phthalic acid anhydride, acylated polyvalent alcohols, more particularly triacetin, ethylene glycol diacetate, and 2,5-diacetoxy-2,5-dihydrofuran are preferred. In addition to or instead of the conventional bleach activators, so-called bleach catalysts can also be incorporated into the textile processing agent. These substances are bleach-enhancing transition metal salts or transition metal complexes such as Mn, Fe, Co, Ru, or Mo salt complexes or carbonyl complexes. Mn, Fe, Co, Ru, Mo, Ti, V, and Cu complexes having nitrogen-containing tripod ligands, as well as Co, Fe, Cu, and Ru ammine complexes, are also usable as bleach catalysts.

Thickeners

The WRC agents may contain thickeners. The thickener can encompass, for example, a polyacrylate thickener, xanthan gum, gellan gum, guar flour, alginate, carrageenan, carboxymethyl cellulose, bentonite, wellan gum, locust bean flour, agar-agar, tragacanth, gum arabic, pectins, polyoses, starch, dextrines, gelatins, and casein. Modified natural substances such as modified starches and celluloses can, however, also be used as thickeners; examples that may be cited here are carboxymethyl cellulose and other cellulose ethers, hydroxyethyl and -propyl cellulose, and seed flour ethers.

Included among the polyacrylate and polymethacrylate thickeners are, for example, the high-molecular-weight homopolymers of acrylic acid crosslinked with a polyalkenyl polyether, more particularly an allyl ether, of sucrose, pentaerythritol, or propylene (INCI name, according to "International Dictionary of Cosmetic Ingredients" of "The Cosmetic, Toiletry and Fragrance Association (CFTA)": Carbomer), which are also referred to as carboxyvinyl polymers. Polyacrylic acids of this kind are obtained from, among other sources, 3V Sigma under the trade name Polygel®, e.g. Polygel DA, and from B.F. Goodrich under the trade name Carbopol®, e.g. Carbopol 940 (molecular weight approx. 4,000,000), Carbopol 941 (molecular weight approx. 1,250,000), or Carbopol 934 (molecular weight approx. 3,000,000). Also included herein are the following acrylic acid copolymers: (i) copolymers of two or more monomers from the group of acrylic acid, methacrylic acid, and their simple esters, formed preferably with $C_{1-4}$ alkanols (INCI: Acrylates Copolymer), included among which are, for example, the copolymers of methacrylic acid, butyl acrylate, and methyl methacrylate (CAS designation according to Chemical Abstracts Service: 25035-69-2), or of butyl acrylate and methyl methacrylate (CAS 25852-37-3), and which are obtainable, for example, from Rohm & Haas under the trade names Aculyn® and Acusol®, and from Degussa (Goldschmidt) under the trade name Tego® Polymer, e.g. the anionic nonassociative polymers Aculyn 22, Aculyn 28, Aculyn 33 (crosslinked), Acusol 810, Acusol 820, Acusol 823, and Acusol 830 (CAS 25852-37-3); (ii) crosslinked high-molecular-weight acrylic acid copolymers, included among which are, for example, the copolymers, crosslinked with an allyl ether of sucrose or of pentaerythritol, of $C_{10-30}$ alkyl acrylates with one or more monomers from the group of acrylic acid, methacrylic acid, and their simple esters formed preferably with $C_{1-4}$ alkanols (INCI: Acrylates/$C_{10-30}$ Alkyl Acrylate Crosspolymer), and which are obtainable, for example, from B.F. Goodrich under the trade name Carbopol®, e.g. the hydrophobized Carbopol ETD 2623 and Carbopol 1382 (INCI: Acrylates/$C_{10-30}$ Alkyl Acrylate Crosspolymer), and Carbopol Aqua 30 (formerly Carbopol EX 473).

A further polymeric thickener preferred for use is xanthan gum, a microbial anionic heteropolysaccharide that is produced by *Xanthomonas campestris* and several other species under aerobic conditions, and has a molecular weight from 2 to 15 million dalton. Xanthan is made up of a chain having β-1,4-bound glucose (cellulose) with side chains. The structure of the subgroups is made up of glucose, mannose, glucuronic acid, acetate, and pyruvate; the number of pyruvate units determines the viscosity of the xanthan gum. More particularly, a fatty alcohol is also suitable as a thickening agent. Fatty alcohols may be branched or unbranched and of natural or petrochemical origin. Preferred fatty alcohols have a carbon chain length of 10 to 20 carbon atoms, preferably 12 to 18. Mixtures of different carbon chain lengths, such as tallow fatty alcohol or coconut fatty alcohol, are preferably used. Examples are Lorol® Spezial ($C_{12-14}$—ROH) or Lorol® Technisch ($C_{12-18}$—ROH) (both from Cognis). Preferred liquid detergents and cleaning agents contain 0.01 to 3% by weight and preferably 0.1 to 1% by weight of the thickener based on the total amount of the agent. The amount of the thickener used depends on the type of thickener and the desired degree of thickening.

Enzymes

The liquid detergents and cleaning agents can contain enzymes, optionally in encapsulated form and/or directly in said detergents and cleaning agents. Suitable enzymes are, in particular, those in the classes of hydrolases, such as proteases, esterases, lipases or lipolytically active enzymes, amylases, cellulases or other glycosyl hydrolases, hemicellulase, cutinases, β-glucanases, oxidases, peroxidases, perhydrolases, oxidoreductases, and/or laccases and mixtures of the aforementioned enzymes. All these hydrolases contribute in the wash to the removal of stains such as protein-, grease-, or starch-containing stains and graying. Moreover, cellulases and other glycosyl hydrolases contribute to color retention and to enhanced textile softness by removing pilling and microfibrils. Oxidoreductases can also be used for bleaching and to inhibit color transfer. Enzymatic active substances obtained from bacterial strains or fungi, such as

*Bacillus subtilis*, *Bacillus licheniformis*, *Streptomyces griseus*, and *Humicola insolens*, are particularly suitable. Proteases of the subtilisin type, and more particularly proteases obtained from *Bacillus lentus*, are preferably used. Enzyme mixtures, for example of protease and amylase or protease and lipase or lipolytically active enzymes, or protease and cellulase, or of cellulase and lipase or lipolytically active enzymes, or of protease, amylase, and lipase or lipolytically active enzymes, or protease, lipase or lipolytically active enzymes and cellulase, but in particular protease- and/or lipase-containing mixtures or mixtures with lipolytically active enzymes, are of particular interest in this context. Examples of such lipolytically active enzymes are the known cutinases. Peroxidases or oxidases have also proven suitable in certain cases. The suitable amylases include, in particular, α-amylases, isoamylases, pullulanases, and pectinases. Cellobiohydrolases, endoglucanases, and β-glucosidases, which are also called cellobiases, and mixtures thereof, are preferably used as cellulases. Because different types of cellulase differ in terms of their CMCase and avicelase activities, the desired activities can be adjusted by means of controlled mixtures of the cellulases.

The enzymes can be adsorbed onto carrier materials in order to protect them from premature breakdown. The proportion of the enzymes, enzyme liquid formulations, enzyme granulates directly contained in the detergents and cleaning agents can be, for example, about 0.01 to 5% by weight, preferably 0.12 to about 2.5% by weight.

However, for example for specific detergents and cleaning agents for consumers with allergies and/or sensitive skin, it can also be preferred that the laundry detergent or cleaning agent does not comprise enzymes.

Electrolytes

A large number of widely varying salts from the group of the inorganic salts can be used as electrolytes. Preferred cations are the alkali and alkaline earth metals; preferred anions are the phosphates and sulfates. From a production engineering standpoint, the use of NaCl or $MgCl_2$ in the detergents and cleaning agents is preferred. The proportion of electrolytes in the detergents and cleaning agents is usually 0.1 to 5% by weight.

Solvents

Nonaqueous solvents that can be used in the liquid detergents and cleaning agents derive, for example, from the group of the monovalent or polyvalent alcohols, alkanolamines, or glycol ethers, provided they are miscible with water in the indicated concentration range. The solvents are preferably selected from ethanol, n- or isopropanol, butanols, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl, or propyl ether, dipropylene glycol monomethyl or -ethyl ether, diisopropylene glycol monomethyl or -ethyl ether, methoxy-, ethoxy-, or butoxytriglycol, 1-butoxyethoxy-2-propanol, 3-methyl-3-methoxybutanol, propylene glycol t-butyl ether, and mixtures of these solvents. Nonaqueous solvents can be used in the liquid detergents and cleaning agents in amounts between 0.5 and 15% by weight, but preferably below 12% by weight and in particular below 9% by weight.

Viscosity

The viscosity of the detergents and cleaning agents can be measured by usual standard methods (e.g. Brookfield LVT-II viscosimeter at 20 rpm und 20° C., spindle 3), and is preferably in the range of 500 to 5000 mPas for liquid detergents. Liquid detergents and cleaning agents preferably have viscosities from 700 to 4000 mPas, with values between 1000 and 3000 mPas being particularly preferred. The viscosity of fabric softeners is preferably 20 to 4000 mPas, with values between 40 and 2000 mPas being particularly preferred. Particularly preferably, the viscosity of fabric softeners is 40 to 1000 mPas.

pH Adjusting Agents

In order to bring the pH of the washing or cleaning agent into the desired range, the use of pH adjusting agents may be indicated. All known acids and bases are usable here, provided their use is not prohibited for environmental or applications-engineering reasons, or for reasons of consumer safety. The quantity of these adjusting agents usually does not exceed 7% by weight of the entire formulation. The pH of liquid detergents and cleaning agents is preferably between 4 and 10, and preferably between 5.5 and 8.5. The pH of liquid fabric softeners is preferably between 1 and 6 and preferably between 1.5 and 3.5.

Dyes

In order to improve the aesthetic impression of the textile treatment agents, they can be colored with suitable dyes. Preferred dyes, the selection of which will present no difficulty whatsoever to the person skilled in the art, possess excellent storage stability and insensitivity to the other ingredients of the detergents and cleaning agents and to light, and no pronounced substantivity with respect to textile fibers, in order not to color them.

Anti-Redeposition Agents

Suitable soil-release polymers, which are also referred to as "anti-redeposition agents", are for example nonionic cellulose ethers such as methyl cellulose and methylhydroxypropyl cellulose having a 15 to 30% by weight concentration of methoxy groups and a 1 to 15% by weight concentration of hydroxypropyl groups, based in each case on the nonionic cellulose ethers, as well as the polymers, known from the prior art, of phthalic acid and/or terephthalic acid or their derivatives, more particularly polymers of ethylene terephthalates and/or polyethylene and/or polypropylene glycol terephthalates or anionically and/or nonionically modified derivatives thereof. Suitable derivatives encompass the sulfonated derivatives of the phthalic acid and terephthalic acid polymers.

Optical Brighteners

Optical brighteners (so-called "whiteners") can be added to the detergents and cleaning agents in order to eliminate graying and yellowing of the treated textile fabrics. These substances absorb onto the fibers and cause brightening and a simulated bleaching effect by converting invisible ultraviolet radiation into longer-wave visible light, the ultraviolet light absorbed from sunlight being emitted as slightly bluish fluorescence and resulting, with the yellow tone of the grayed or yellowed laundry, in pure white. Suitable compounds derive, for example, from the substance classes of the 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalic acid imides, benzoxazole, benzisoxazole, and benzimidazole systems, and pyrene derivatives substituted with heterocycles. The optical brighteners are usually used in quantities of between 0 and 0.3% by weight based on the total weight of the finished detergents and cleaning agents.

Graying Inhibitors

Graying inhibitors have the task of keeping the dirt released from the fiber suspended in the bath and thus preventing reuptake of the dirt. Water-soluble colloids usually of an organic nature are suitable for this purpose, e.g., glue, gelatin, salts of ether carboxylic acids or ether sulfonic acids of starch or cellulose or salts of acidic sulfuric acid esters of cellulose or starch. Water-soluble polyamides containing acid groups are also suitable for this purpose. In addition, soluble starch preparations and starch products other than those mentioned above may also be used, e.g., degraded starch, aldehyde starches, etc. Polyvinylpyrrolidone may also be used. However, cellulose ethers such as carboxymethylcellulose (sodium salt), methylcellulose, hydroxyalkylcellulose and mixed ethers such as methylhydroxyethylcellulose, methylhydroxypropylcellulose, methylcarboxymethylcellulose and mixtures thereof as well as polyvinylpyrrolidone are preferred, e.g., in amounts of 0.1% by weight to 5% by weight, based on the agent.

Anti-Wrinkle Agents

Because textile fabrics, in particular, those made of rayon, viscose, cotton, and mixtures thereof, can tend to wrinkle due to the individual fibers being sensitive to bending, kinking, pressing, and squeezing perpendicularly to the fiber direction, the detergents and cleaning agents can contain synthetic anti-wrinkle agents. These include, for example, synthetic products based on fatty acids, fatty acid esters, fatty acid amides, fatty acid alkylol esters, or fatty acid alkylolamides, or fatty alcohols that are usually reacted with ethylene oxide, or products based on lecithin or modified phosphoric acid esters.

Antimicrobial Active Substances

In order to counteract microorganisms, the detergents and cleaning agents can contain antimicrobial active substances. A distinction is made here, depending on the antimicrobial spectrum and mechanism of action, between bacteriostatics and bactericides, fungistatics and fungicides, etc. Examples of important substances from these groups include benzalkonium chlorides, alkylarylsulfonates, halogen phenols, and phenol mercuric acetate, with it being possible to dispense with these compounds entirely in the detergents and cleaning agents according to the invention.

Preservatives

The detergents and cleaning agents according to the present invention can contain preservatives, with only those that possess little or no skin-sensitizing potential preferably being used. Examples include sorbic acid and its salts, benzoic acid and its salts, salicylic acid and its salts, phenoxyethanol, formic acid and its salts, 3-iodo-2-propynyl-butyl carbamate, sodium N-(hydroxymethyl)glycinate, biphenyl-2-ol, and mixtures thereof. A suitable preservative is illustrated by the solvent-free, aqueous combination of diazolidinyl urea, sodium benzoate and potassium sorbate (available as Euxyl® K 500 from Schuelke and Mayr), which can be used in a pH range of up to 7. Preservatives based on organic acids and/or the salts thereof are particularly suitable for preservation of the skin-friendly detergents and cleaning agents according to the invention.

Antioxidants

The detergents and cleaning agents can contain antioxidants in order to prevent undesirable changes caused by oxygen and other oxidative processes to the detergents and cleaning agents and/or the treated textile fabrics. This class of compounds includes, for example, substituted phenols, hydroquinones, pyrocatechols and aromatic amines as well as organic sulfides, polysulfides, dithiocarbamates, phosphites, phosphonates and vitamin E.

Antistatics

Increased wear comfort can result from the additional use of antistatics that can be included in the detergents and cleaning agents. Antistatics increase the surface conductivity and thereby allow improved discharge of built-up charges. Generally, antistatics are substances with at least one hydrophilic molecule ligand and provide a more or less hygroscopic film on the surfaces. These mainly interface active antistatics can be subdivided into nitrogen-containing (amines, amides, quaternary ammonium compounds), phosphorus-containing (phosphoric acid esters) and sulfur-containing (alkyl sulfonates, alkyl sulfates) antistatics. Lauryl (or stearyl) dimethyl benzyl ammonium chlorides are suitable antistatics for textile fabrics or as additives to detergents and cleaning agents, resulting in an additional softening effect.

Foam Inhibitors

Silicone derivatives, for example, can be incorporated into the textile treatment agents to improve the re-wettability of the treated textile fabrics and to facilitate ironing of the treated textile fabrics. By means of their foam-inhibiting properties, they additionally improve the final rinse behavior of the detergents and cleaning agents. Preferred silicone derivatives are polydialkylsiloxanes or alkylarylsiloxanes, in which the alkyl groups possess one to five carbon atoms and are totally or partially fluorinated. Preferred silicones are polydimethylsiloxanes that can be optionally derivatized and then are aminofunctional or quaternized or possess Si—OH, Si—H and/or Si—Cl bonds. The viscosities of the preferred silicones at 25° C. are in the range of 100 to 100,000 mPas, wherein the silicones can be used in amounts of between 0.2 and 5% by weight based on the total detergents and cleaning agents.

UV Absorbers

Finally, the detergents and cleaning agents can also contain UV absorbers that are absorbed onto the surface of the treated textiles and improve the light-fastness of the fibers. Compounds that exhibit these desired properties are, for example, the compounds that act by radiationless deactivation, and derivatives of benzophenone having substituents in the 2- and/or 4-position. Also suitable are substituted benzotriazoles, acrylates phenyl-substituted in the 3-position (cinnamic acid derivatives) optionally having cyano groups in the 2-position, salicylates, organic Ni complexes, and natural substances such as umbelliferone and endogenous urocanic acid.

Heavy Metal Complexing Agents

Substances that complex heavy metals can be used in order to avoid the heavy-metal-catalyzed breakdown of certain laundry-detergent ingredients. Suitable heavy metal complexing agents are, for example, the alkali salts of ethylenediaminetetraacetic acid (EDTA) or of nitrilotriacetic acid (NTA), as well as alkali-metal salts of anionic polyelectrolytes such as polymaleates and polysulfonates. A preferred class of complexing agents is the phosphonates, which are contained in preferred liquid laundry detergents and cleaning agents in quantities from 0.01 to 2.5% by weight, preferably 0.02 to 2% by weight, and in particular from 0.03 to 1.5% by weight. These preferred compounds include, in particular, organophosphonates such as 1-hydroxyethane-1,1-diphosphonic acid (HEDP), aminotri(methylenephosphonic acid) (ATMP), diethylenetriamine penta(methylenephosphonic acid) (DTPMP or DETPMP), and 2-phosphonobutane-1,2,4-tricarboxylic acid (PBS-AM), which are usually used in the form of their ammonium or alkali-metal salts.

Production of the Preparations

The production of solid WRC agents can be carried out by conventional methods such as the tower spraying method, fluidized bed granulation, agglomeration, powder mixing, tableting, and granulation, more particularly SKET granulation.

The production of liquid WRC agents is also carried out by means of common and known methods and processes, for example by simply mixing the components in stirred reactors, with water, non-aqueous solvents and surfactants being prepared as appropriate and the additional components then being added by portions. In this manner, liquid detergents and cleaning agents can be produced by first preparing components such as the linear alkyl sulfonates, citric acid, boric acid, phosphonic acid, fatty alcohol ether sulfates, etc., and nonionic surfactants. The solvent components are preferably also added at this point, but they can also be added at a later time. The thickener, such as a polyacrylate, can then be added to these components. A base such as NaOH, KOH, triethanolamine or monoethanolamine, followed by the fatty acid if present, is then added. After this, the remaining ingredients and the remaining solvents of the aqueous liquid detergent and cleaning agent are added to the mixture, and the pH is adjusted to about 8.5. Finally, the particles to be dispersed can be added, and by mixing, homogeneously distributed in the aqueous liquid detergents and cleaning agents.

Cosmetic Preparations and Body Care Products

The cosmetic agents and/or body care products according to the invention may comprise other typical auxiliaries and additives, such as mild surfactants, oil components, emulsifiers, pearlizing waxes, bodying agents, thickeners, superfatting agents, stabilizers, polymers, silicone compounds, fats, waxes, lecithins, phospholipids, UV protection factors, humectants, biogenic active ingredients, antioxidants, repellants, self-tanning agents, tyrosine inhibitors (depigmenting agents), hydrotropes, solubilizers, preservatives, perfume oils and dyes and the like.

Surfactants

As surface-active substances, anionic, nonionic, cationic and/or amphoteric or zwitterionic surfactants whose content of the agents is ordinarily approximately 1 to 70, preferably 5 to 50, and in particular 10 to 30% by weight may be included. Typical examples of anionic surfactants are soaps, alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and the salts thereof, fatty acid isethionates, fatty acid sarcosinates, fatty acid taurides, N-acylamino acids such as acyl lactylates, acyl tartrates, acyl glutamates, and acyl aspartates, alkyl oligoglucoside sulfates, protein fatty acid condensation products (in particular wheat-based plant products) and alkyl (ether) phosphates. If the anionic surfactants contain polyglycol ether chains, these may exhibit a conventional, but preferably a narrowed homolog distribution. Typical examples of nonionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid N-alkyl glucamides, protein hydrolysates (in particular wheat-based plant products), polyol fatty acid esters, sugar esters, sorbitan esters, polysorbates and amine oxides. If the nonionic surfactants contain polyglycol ether chains, these may exhibit a conventional, but preferably a narrowed homolog distribution. Typical examples of cationic surfactants are quaternary ammonium compounds such as dimethyl distearylammonium chloride, and esterquats, in particular quaternized fatty acid trialkanolamine ester salts. Typical examples of amphoteric or zwitterionic surfactants are alkyl betaines, alkylamidobetaines, aminopropionates, aminoglycinates, imidazolinium betaines and sulfobetaines. The above-mentioned surfactants are exclusively known compounds. Typical examples of particularly suitable mild surfactants, i.e. particularly gentle to the skin, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkyl amidobetaines, amphoacetals and/or protein fatty acid condensates, the latter preferably based on wheat proteins.

Oil Components

Examples of suitable oil components include Guerbet alcohols based on fatty alcohols with 6 to 18, and preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, in particular 2-ethyl hexanol, esters of $C_{18}$-$C_{38}$ alkyl hydroxycarboxylic acids with linear or branched $C_6$-$C_{22}$ fatty alcohols, in particular dioctyl malate, esters of linear and/or branched fatty acids with multivalent alcohols (such as propylene glycol, dimer diol or trimer triol) and/or Guerbet alcohols, triglycerides based on $C_6$-$C_{10}$ fatty acids, liquid mono/di/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates such as dicaprylyl carbonate (Cetiol® CC), Guerbet carbonates based on fatty alcohols with 6 to 18, and preferably 8 to 10 carbon atoms, esters of benzoic acid with linear and/or branched $C_6$-$C_{22}$ alcohols (e.g. Finsolv® TN), linear or branched, symmetrical or asymmetrical dialkyl ethers with 6 to 22 carbon atoms per alkyl group such as dicaprylyl ether (Cetiol® OE), ring-opening products of epoxidized fatty acid esters with polyols, silicone oils (cyclomethicones, silicone methicone types, etc.) and/or aliphatic or naphthenic hydrocarbons such as squalane, squalene, or dialkyl cyclohexanes.

Emulsifiers

Emulsifiers which may be used are for example nonionogenic surfactants from at least one of the following groups:

addition products of 2 to 30 mol of ethylene oxide and/or 0 to 5 mol of propylene oxide onto linear fatty alcohols with 8 to 22 carbon atoms, fatty acids with 12 to 22 carbon atoms, alkyl phenols with 8 to 15 carbon atoms in the alkyl group, as well as alkylamine with 8 to 22 carbon atoms in the alkyl radical;

alkyl and/or alkenyl oligoglycosides with 8 to 22 carbon atoms in the alk(en)yl radical and ethoxylated analogs thereof;

addition products of 1 to 15 mol of ethylene oxide onto castor oil and/or hardened castor oil;

addition products of 15 to 60 mol of ethylene oxide onto castor oil and/or hardened castor oil;

partial esters of glycerol and/or sorbitan with unsaturated, linear or saturated, branched fatty acids having 12 to 22 carbon atoms and/or hydroxycarboxylic acids having 3 to 18 carbon atoms, and adducts thereof with 1 to 30 mol of ethylene oxide;

partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof with 1 to 30 mol of ethylene oxide;

mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers or corresponding derivatives;

block copolymers, e.g. polyethylene glycol-30 dipolyhydroxystearates;

polymer emulsifiers, e.g. Pemulen® grades (TR-1, TR-2) from Goodrich or Cosmedia® SP from Cognis;

polyalkylene glycols and glycerol carbonate.

In the following, particularly suitable emulsifiers are discussed in further detail:

Alkoxylates. The addition products of ethylene oxide and/or propylene oxide onto fatty alcohols, fatty acids, alkyl phenols or castor oil are known, commercially available products. These are homologous mixtures whose average degree of alkoxylation corresponds to the ratio of the amounts of ethylene oxide and/or propylene oxide and substrates with which the addition reaction is carried out. $C_{12/18}$ fatty acid mono- and diesters of addition products of ethylene oxide to glycerol are known as refatting agents for cosmetic preparations.

Alkyl and/or alkenyl oligoglycosides. Alkyl and/or alkenyl oligoglycosides, their production, and their use are known from the prior art. They are produced in particular by reacting glucose or oligosaccharides with primary alcohols with 8 to 18 carbon atoms. With respect to the glycoside radical, both monoglycosides, in which a cyclic sugar radical is glycosidically bonded to the fatty alcohol, and oligomeric glycosides with a preferred degree of oligomerization of approximately 8 are suitable. Here, the degree of oligomerization is a statistical average value upon which a homolog distribution common for such technical products is based.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, as well as technical mixtures thereof, which can contain minor subordinate amounts of triglycerides from the production process. Addition products of 1 to 30, and preferably 5 to 10 mol of ethylene oxide onto the aforementioned partial glycerides are also suitable.

Sorbitan esters. Examples of suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, as well as technical mixtures thereof. Addition products of 1 to 30, and preferably 5 to 10 mol of ethylene oxide onto the aforementioned sorbitan esters are also suitable.

Polyglycerol esters. Typical examples of suitable polyglycerol esters are polyglyceryl-2-dipolyhydroxystearate (Dehymuls® PGPH), polyglycerol-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methyl glucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters, optionally reacted with 1 to 30 mol of ethylene oxide, are mono-, di- and triesters of trimethylolpropane or pentaerythritol with lauric acid, coconut fatty acid, tallow fatty acid, palmitic acid, stearic acid, oleic acid, behenic acid and the like.

Anionic emulsifiers. Typical anionic emulsifiers are aliphatic fatty acids with 12 to 22 carbon atoms, such as palmitic acid, stearic acid, or behenic acid, as well as dicarboxylic acids with 12 to 22 carbon atoms such as azelaic acid or sebacic acid.

Amphoteric and cationic emulsifiers. In addition, zwitterionic surfactants may be used as emulsifiers. Zwitterionic surfactants are those surface-active compounds which bear at least one quaternary ammonium group and at least one carboxylate and one sulfonate group per molecule. Particularly suitable zwitterionic surfactants are the so-called betaines such as N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxylmethyl-3-hydroxyethyl imidazolines, with in each case 8 to 18 carbon atoms in the alkyl or acyl group and cocoacylaminoethylhydroxyethylcarboxymethyl glycinate. Particularly preferred is the fatty acid amide derivative known by the CTFA name cocamidopropyl betaine. Ampholytic surfactants are also suitable emulsifiers. Ampholytic surfactants are understood to refer to those surface-active compounds which, in addition to one $C_{8/18}$-alkyl or acyl group per molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants may also be considered as emulsifiers, with those of the esterquat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes include natural waxes, for example candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also referred to as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Cooling Substances

Cooling substances are compounds that produce a feeling of coolness on the skin. As a rule, these are menthol compounds which—in addition to the parent substance menthol itself—are selected for example from the group consisting of menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849) and the menthane carboxylic acid esters and amides WS-3, WS-4, WS-5, WS-12, WS-14 and WS-30 and mixtures thereof.

[1]FEMA stands for "Flavor and Extracts Manufacturers Association" and GRAS is defined as "Generally Regarded As Safe". A FEMA GRAS designation means that the substance designated such has been tested according to standard methods and is considered to be toxicologically safe.

A first important representative of these substances is monomenthyl succinate (FEMA GRAS 3810). Both the succinate and also the analogue monomenthyl glutarate (FEMA GRAS 4006) are important representatives of monomenthyl esters on the basis of di- and polycarboxylic acids:

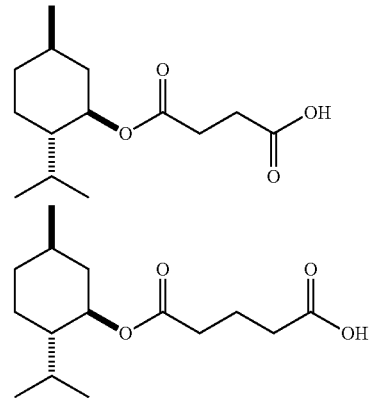

Examples of applications of these substances are available, for example, in the publications WO 2003 043431 (Unilever) or EP 1332772 A1 (IFF).

The next important group of preferred menthol compounds within the meaning of the invention comprises carbonate esters of menthol and polyols such as glycols, glycerol or carbohydrates such as menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives.

The menthol compounds menthyl lactate (FEMA GRAS 3748=Frescolat® ML) and, particularly, menthone glyceryl acetal (FEMA GRAS 3807) or, respectively, menthone glyceryl ketal (FEMA GRAS 3808), which is marketed under the trade name Frescolat® MAG, are also preferred. Among these substances, menthone glyceryl acetal/ketal, menthyl lactate, and menthol ethylene glycol carbonate or menthol propylene glycol carbonate, which are marketed by the applicant under the names Frescolat® MGA, Frescolat® ML, Frescolat® MGC, and Frescolat® MPC, have been found to be most particularly advantageous.

Menthol compounds, which have a C—C bond in the 3 position and also have a number of representatives suitable for use, were first developed in the 1970s. These substances are generally referred to as the WS type. The parent substance is a menthol derivative in which the hydroxyl group is replaced by a carboxyl group (WS-1). All other WS types are derived from this structure, such as the preferred species WS-3, WS-4, WS-5, WS-12, WS-14 and WS-30.

Consistency Factors and Thickeners

The bodying agents mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil grades (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinyl pyrrolidone. Other bodying agents which have proved to be particularly effective are bentonites, for example Bentone® Gel VS-5PC (Rheox) which is a mixture of cyclopentasiloxane, Disteardimonium Hectorite and propylene carbonate. Other suitable bodying agents are surfactants such as ethoxylated fatty acid glycerides, esters of fatty acids with polyols, for example pentaerythritol or trimethylol propane, narrow-range fatty alcohol ethoxylates or alkyl oligoglucosides and electrolytes such as sodium chloride and ammonium chloride.

Superfatting Agents and Stabilizers

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Metal salts of fatty acids such as magnesium, aluminium and/or zinc stearate or ricinoleate may be used as stabilizers.

Polymers

Suitable cationic polymers are, for example, cationic cellulose derivatives such as the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as Luviquat® (BASF), condensation products of polyglycols and amines, quaternized collagen polypeptides such as Lauryldimonium hydroxypropyl hydrolyzed Collagen (Lamequat®L, Grünau), quaternized wheat polypeptides, polyethyleneimine, cationic silicone polymers such as amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as quaternized chitosan, optionally in microcrystalline distribution, condensation products of dihaloalkyls, for example dibromobutane, with bis-dialkylamines, for example bis-dimethylamino-1,3-propane, cationic guar gum such as Jaguar®CBS, Jaguar®C-17, Jaguar®C-16 from Celanese, quaternized ammonium salt polymers such as Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors

UV protection factors are, for example, organic substances (light filters) which are liquid or crystalline at room temperature and which are capable of absorbing ultraviolet radiation and of releasing the energy absorbed in the form of longer-wave radiation, for example, heat. UV protection factors are usually present in amounts of 0.1 to 5 and, preferably, 0.2 to 1% by weight. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (octocrylene);

esters of salicylic acid, preferably salicylic acid-2-ethylhexyl ester, salicylic acid-4-isopropylbenzyl ester, salicylic acid homomethyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as 2,4,6-trianilino-(p-carbo-2'-ethyl-1'-hexyloxy)-1,3,5-triazine and octyl triazone, or dioctyl butamido triazone (Uvasorb® HEB);

propane-1,3-diones such as 1-(4-tert-butylphenyl)-3-(4'-methoxyphenyl)-propane-1,3-dione;

ketotricyclo(5.2.1.0)decane derivatives.

Suitable water-soluble substances are:

2-phenylbenzimidazole-5-sulfonic acid and alkali metal, alkaline earth metal, ammonium, alkylammonium, alkanolammonium and glucammonium salts thereof;

1H-benzimidazole-4,6-disulfonic acid, 2,2'-(1,4-phenylene)bis-, disodium salt (Neo Heliopan® AP)

sulfonic acid derivatives of benzophenones, preferably 2-hydroxy-4-methoxybenzophenone-5-sulfonic acid and salts thereof;

sulfonic acid derivatives of 3-benzylidene camphor such as 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as 1-(4'-tert-butylphenyl)-3-(4'-methoxyphenyl)-propane-1,3-dione, 4-tert-butyl-4'-methoxydibenzoyl methane (Parsol® 1789), 2-(4-Diethylamino-2-hydroxybenzoyl)-benzoic acid hexylester (Uvinul® A Plus), 1-phenyl-3-(4'-isopropylphenyl)-propane-1,3-dione and enamine compounds. The UV-A and UV-B filters may of course also be used in the form of mixtures. Particularly favorable combinations consist of the derivatives of benzoyl methane, for example 4-tert-butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as 2-phenylbenzimidazole-5-sulfonic acid and alkali metal, alkaline earth metal, ammonium, alkylammonium, alkanolammonium and glucammonium salts thereof.

In addition to the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape, although ellipsoidal particles or other non-spherical particles may also be used. The pigments may also be surface-treated, i.e. hydrophilized or hydrophobized. Typical examples are coated titanium dioxides, for example Titandioxid T 805 (Degussa) or Eusolex® T2000, Eusolex® T, Eusolex® T-ECO, Eusolex T-S, Eusolex T-Aqua, Eusolex T-45D (all from Merck), Uvinul $TiO_2$ (BASF). Suitable hydrophobic coating materials are, above all, silicones and, among these, especially trialkoxyoctylsilanes or simethicones. So-called micro- or nanopigments are preferably used in sun protection products. Micronized zinc oxide such as Z-COTE® or Z-COTE HP1® is preferably used.

Moisturizers

Moisturizers are added to improve the sensory properties of the composition as well as to regulate skin hydration. At the same time, the stability in cold temperatures of the compositions according to the invention is increased, particularly in emulsions. Moisturizers are typically present in quantities of 0.1 to 15% by weight, preferably, 1 to 10% by weight, and more particularly 5 to 10% by weight.

Suitable humectants according to the invention include amino acids, pyrrolidone carbonic acid, lactic acid and its salts, lactitol, urea and urea derivatives, ureic acid, glucosamine, creatinine, hydrolysis products of collagen, chitosan or chitosan salts/-derivatives, and in particular polyols and polyol derivatives (e.g. glycerol, diglycerol, triglycerol, ethylene glycol, propylene glycol, butylene glycol, erythrite, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugar and sugar derivatives (including fructose, glucose, maltose, maltitol, mannite, inosite, sorbite, sorbityl silanediol, sucrose, trehalose, xylose, xylitol, glucuronic acid and its salts), ethoxylated sorbitol (Sorbeth-6, Sorbeth-20, Sorbeth-30, Sorbeth-40), honey and hydrogenated honey, hydrogenated starch hydrolysates, as well as mixtures of hydrogenated wheat protein and PEG-20-acetate copolymers. Particularly preferred humectants according to the invention are glycerine, diglycerine, triglycerine and butylene glycol.

Biogenic Agents and Antioxidants

Biogenic agents are, for example, tocopherol, tocopherol acetate, tocopherol palmitate, ascorbic acid, (deoxy)ribonucleic acid and fragmentation products thereof, 3-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Antioxidants interrupt the photo-chemical reaction chain which is triggered as soon as UV radiation enters the skin. Typical examples are amino acids (for example glycine, histidine, tyrosine, tryptophane) and derivatives thereof, imidazoles (for example urocanic acid) and derivatives thereof, peptides such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also (metal) chelators (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate), and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Deodorants and Antimicrobial Agents

Cosmetic deodorants (anti-odor agents) counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents.

Antimicrobial Agents.

Suitable antimicrobial agents are, in principle, all substances effective against Gram-positive bacteria, such as 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethylphenol, 2,2'-methylene-bis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), and salicylic acid N-alkylamides, such as n-octyl-salicylamide or n-decylsalicylamide.

Enzyme Inhibitors.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Odor Absorbers.

Suitable odor absorbers are substances which are able to absorb and largely retain odor-forming compounds. They lower the partial pressure of the individual components, thus also reducing their rate of diffusion. It is important that perfumes must remain unimpaired in this process. Odor absorbers are not effective against bacteria. They comprise, for example, as their main constituent, a complex zinc salt of ricinoleic acid or specific, largely odor-neutral fragrances which are known to the person skilled in the art as "fixatives", such as extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants.

Antiperspirants (antitranspirants) reduce perspiration and thus counteract underarm wetness and body odor by influencing the activity of the eccrine sweat glands. Aqueous or water-free antiperspirant formulations typically contain the following ingredients:

astringent active ingredients,
oil components,
nonionic emulsifiers,
co-emulsifiers,
bodying agents,
auxiliaries in the form of, for example, thickeners or complexing agents and/or
non-aqueous solvents such as ethanol, propylene glycol and/or glycerol:

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine. Oil-soluble and water-soluble auxiliaries typically encountered in antiperspirants may also be present in relatively small amounts. Such oil-soluble auxiliaries include, for example:

inflammation-inhibiting, skin-protecting or pleasant-smelling essential oils,
synthetic skin-protecting agents and/or
oil-soluble perfume oils.

Common water-soluble auxiliaries are, for example, preservatives, water-soluble fragrances, pH adjustment agents, for example, buffer mixtures, water-soluble thickeners, for example, water-soluble natural or synthetic polymers such as xanthan gum, hydroxyethyl cellulose, polyvinyl pyrrolidone or high molecular polyethylene oxides.

Film Formers

Common film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Active Ingredients

Examples of suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicylic acid (or in combination with hexachlorophene), undecylenic acid monoethanolamide sulfosuccinate sodium salt, Lamepon® UD (protein-undecylenic acid condensate), zinc pyrithione, aluminum pyrithione and magnesium pyrithione/dipyrithione magnesium sulfate.

Swelling Agents

Montmorillonites, clay minerals, Pemulen, and alkyl-modified Carbopol grades (Goodrich) may be used as swelling agents for aqueous phases. Further suitable polymers or swelling agents are given in the overview by R. Lochhead in Cosm. Toil. 108, 95 (1993).

Insect Repellents

Examples of suitable insect repellents include N,N-diethyl-m-toluamide, 1,2-pentanediol, or ethyl butylacetylaminopropionate. A suitable self-tanning agent is dihydroxyacetone. Examples of suitable tyrosine inhibitors, which prevent the formation of melanin and are used in depigmenting agents, include arbutin, ferulic acid, kojic acid, coumaric acid, and ascorbic acid (vitamin C).

Ingredients for Oral and Dental Care

Toothpastes or tooth creams are generally understood as being gel-like or pasty preparations comprising water, thickeners, humectants, abrasive or cleaning agents, surfactants, sweeteners, flavorings, deodorizing active ingredients and active ingredients against oral and tooth diseases. All conventional cleaning agents, such as chalk, dicalcium phosphate, insoluble sodium metaphosphate, aluminium silicates, calcium pyrophosphate, fine particulate synthetic resins, silicas, aluminium oxide and aluminium oxide trihydrate, can be used in the toothpastes according to the invention.

Preferred suitable cleaning bodies for the toothpastes according to the invention are primarily fine particulate xerogel silicas, hydrogel silicas, precipitated silicas, aluminium oxide trihydrate and fine particulate alpha-aluminium oxide or mixtures of these cleaning bodies in amounts of from 15 to 40% by weight of the toothpaste. Suitable humectants are predominantly low molecular weight polyethylene glycols, glycerol, sorbitol or mixtures of these products in amounts of up to 50% by weight. Among the known thickeners, the thickening, fine particulate gel silicas and hydrocolloids, such as carboxymethylcellulose, hydroxyethylcellulose, hydroxypropyl guar, hydroxyethyl starch, polyvinylpyrrolidone, high molecular weight polyethylene glycol, plant gums such as tragacanth, agar agar, carrageenan moss, gum arabic, xanthan gum and carboxyvinyl polymers (e.g. Carbopol® grades) are suitable. In addition to the mixtures of menthofuran and menthol compounds, the oral and dental care compositions can in particular comprise surface-active substances, preferably anionic and nonionic high-foaming surfactants, such as the substances already listed above, but in particular alkyl ether sulphate salts, alkyl polyglycosides and mixtures thereof.

Further common toothpaste additives are:
preservatives and antimicrobial substances such as p-hydroxybenzoic acid methyl, ethyl or propyl ester, sodium sorbate, sodium benzoate, bromochlorophen, phenylsalicylic acid esters, thymol and the like;
anti-tartar active ingredients, e.g. organophosphates such as 1-hydroxyethane-1,1-diphosphonic acid, 1-phosphonopropane-1,2,3-tricarboxylic acid and others, which are known e.g. from U.S. Pat. No. 3,488,419, DE 2224430 A1 and DE 2343196 A1;
other caries-inhibiting substances such as sodium fluoride, sodium monofluorophosphate, tin fluoride;
sweeteners, such as saccharin sodium, sodium cyclamate, sucrose, lactose, maltose, fructose or Aspartame® (L-aspartyl-L-phenylalanine methyl ester), Stevia extracts or sweetening constituents thereof, in particular Ribeaudioside;
additional flavoring agents such as eucalyptus oil, anise oil, fennel oil, caraway oil, methyl acetate, cinnamaldehyde, anethol, vanillin, thymol, and mixtures of these and other natural and synthetic flavoring agents;
pigments such as titanium dioxide;
dyes;
buffer substances such as primary, secondary or tertiary alkali metal phosphates or citric acid/sodium citrate;
wound-healing and anti-inflammatory substances such as allantoin, urea, azulene, chamomile active ingredients and acetylsalicylic acid derivatives.

A preferred embodiment of the cosmetic preparations is toothpastes in the form of an aqueous, pasty dispersion, comprising polishing agents, humectants, viscosity regulators and optionally further common components, as well as the mixture of menthofuran and menthol compounds in amounts of 0.5 to 2% by weight.

In mouthwashes, a combination with aqueous-alcoholic solutions of varying concentration gradients of essential oils, emulsifiers, astringent and toning drug extracts, tartar-preventing, antibacterial additives and taste correctives is directly possible. A further preferred embodiment of the invention is a mouthwash in the form of an aqueous or aqueous-alcoholic solution comprising the mixture of menthofuran and menthol compounds in amounts of 0.5 to 2% by weight. In mouthwashes which are diluted prior to use, adequate effects can be achieved with higher concentrations corresponding to the intended dilution ratio.

Hydrotropes

In order to improve flow behavior, hydrotropes such as ethanol, isopropyl alcohol, or polyols can be used; these substances largely correspond to the carriers specified above. Polyols which are suitable here preferably have 2 to 15 carbon atoms and at least two hydroxyl groups. The polyols can also contain further functional groups, in particular amino groups, or be modified with nitrogen. Typical examples are:
glycerol;
alkylene glycols, such as ethylene glycol, diethylene glycol, propylene glycol, butylene glycol, hexylene glycol, and polyethylene glycols with an average molecular weight of 100 to 1000 daltons;
technical-grade oligoglycerol mixtures with an intrinsic degree of condensation of 1.5 to 10 such as technical-grade diglycerol mixtures with a diglycerol content of 40 to 50% by weight;

methylol compounds, more particularly trimethylolethane, trimethylolpropane, trimethylol-butane, pentaerythritol, and dipentaerythritol;

lower alkyl glucosides, more particularly those with 1 to 8 carbon atoms in the alkyl radical, such as methyl and butyl glucoside;

sugar alcohols with 5 to 12 carbon atoms, such as sorbitol or mannitol, sugars with 5 to 12 carbon atoms, such as glucose or saccharose;

amino sugars such as glucamine;

dialcohol amines, such as diethanolamine or 2-amino-1, 3-propanediol.

guar compounds for the stabilizing of aqueous dispersions that contain perfume oils and encapsulated fragrances and on the other to the use of production of cosmetic preparations and detergents and cleaning agents according to the invention, with the amount contained preferably being about 0.1 to about 5% by weight and more particularly about 0.5 to about 2% by weight.

EXAMPLES

Production Examples

Model formulations are given in Table 1 below; all amounts indicated are to be understood as % by weight.

TABLE 1

| FORMULATIONS | 1 | 2 | 3 | 4 | 5 | 6 | 7 | 8 |
|---|---|---|---|---|---|---|---|---|
| Fragrance SOFT SHINE 985365 | 70 | 70 | 70 | 70 | | | | |
| Fragrance STAR TREK 987648 | | | | | 70 | 70 | 70 | 70 |
| Fragrance 985272 BLUE JOY | | | | | | | | |
| Symcap ® K2LD | 20 | | | | 20 | | | |
| Symcap ® G | | 20 | | | | 20 | | |
| Symcap ® FS ST | | | 20 | | | | 20 | |
| Symcap ® K FS | | | | 20 | | | | 20 |
| Solubilizer 660352 | | 0.1 | 0.1 | | | 0.2 | 0.2 | |
| Water | | | | to 100 | | | | |
| Esaflor HM 22 Powder | 0.05 | 0.08 | 0.05 | 0.1 | 0.06 | 0.1 | 0.06 | 0.1 |
| FORMULATIONS | 9 | 10 | 11 | 12 | 13 | 14 | 15 | 16 |
| Fragrance SOFT SHINE 985365 | | | | | 80 | 80 | 80 | 80 |
| Fragrance STAR TREK 987648 | | | | | | | | |
| Fragrance 985272 BLUE JOY | 70 | 70 | 70 | 70 | | | | |
| Symcap ® K2LD | 20 | | | | 10 | | | |
| Symcap ® G | | 20 | | | | 10 | | |
| Symcap ® FS ST | | | 20 | | | | 10 | |
| Symcap ® K FS | | | | 20 | | | | 10 |
| Solubilizer 660352 | | 0.1 | 0.1 | | | 0.05 | 0.08 | |
| Water | | | | to 100 | | | | |
| Esaflor HM 22 Powder | 0.05 | 0.06 | 0.06 | 0.05 | 0.05 | 0.07 | 0.05 | 0.05 |

Preservatives

Examples of suitable preservatives include phenoxyethanol, formaldehyde solution, parabens, pentane diol, or sorbic acid as well as the silver complexes known under the name Surfacine® and the other substance classes listed in Annex 6, Part A and B of the Cosmetics Directive.

Dyes

Substances that are suitable and approved for cosmetic purposes can be used as dyes, such as those listed in the publication "Cosmetic Coloring Agents" of the Colorant Commission of the German Research Foundation, Verlag Chemie, Weinheim, 1984, pp. 81-106. Examples include Cochineal Red A (C.I. 16255), Patent Blue V (C.I. 42051), indigotin (C.I. 73015), chlorophyllin (C.I. 75810), Quinoline Yellow (C.I. 47005), titanium dioxide (C.I. 77891), Indanthrene Blue RS (C.I. 69800) and madder lake (C.I. 58000). Luminol can also be included as a luminescent dye. These dyes are ordinarily used in concentrations of 0.001 to 0.1% by weight, relative to the total mixture.

The total amount of the auxiliary substances and additives can be 1 to 50, and preferably 5 to 40% by weight relative to the dyes. The production of the dyes can be carried out by common cold or hot processes; the phase inversion temperature method is preferred.

Uses

Further subject matter of the invention relates on the one hand to the use of hydrophobically modified hydroxyalkyl Production: Prepare the perfume oil, and then add remaining components in the order indicated while stirring (propeller stirrer). Stir until a homogenous mixture is obtained.

Application Examples

Dispersions 1 through 8 according to the invention and comparative dispersions V1 and V2 were stored for a period of 6 weeks at 5, 20 and 40° C. respectively.

Capsule types A through D were used. The capsules were produced according to methods commonly known to the person skilled in the art; the following are the respective substances of which the capsule shells were composed:

Capsule A: melamine-formaldehyde resin (Symcap FS ST)
Capsule B: melamine-formaldehyde resin (Symcap K LD)
Capsule C: melamine-formaldehyde resin (Symcap K FS<)
Capsule D: Polyurethane (Symcap G)

The stability of the formulations was optically assessed, more particularly with respect to homogeneity of the phase. This assessment was carried out according to the following classification:

(+++)=no phase separation,
(++)=minor phase separation,
(+)=clear phase separation,
(0)=strong phase separation.

The results are summarized in Tables 2a and 2b:

TABLE 2A

Stability test - Composition of the dispersions

| Composition of dispersion | 1 | 2 | 3 | 4 | 5 | 6 | 7 | 8 | V1 | V2 |
|---|---|---|---|---|---|---|---|---|---|---|
| Citrus oil | 60.0 | 70.0 | 60.0 | 70.0 | 60.0 | 70.0 | 60.0 | 70.0 | 60.0 | 70.0 |
| Symcap FS ST | 15.0 | 10.0 | — | — | — | — | — | — | — | — |
| B) Symcap K LD | — | — | 15.0 | 10.0 | — | — | — | — | 15.0 | 10.0 |
| C) Symcap K FS | — | — | — | — | 15.0 | 10.0 | — | — | — | — |
| D) Symcap G | — | — | — | — | — | — | 15.0 | 10.0 | — | — |
| ESAFLOR HM22 | 0.05 | 0.05 | 0.05 | 0.05 | 0.05 | 0.05 | 0.05 | — | — | — |
| Water to 100 | | | | | to 100 | | | | | |

TABLE 2B

Stability test - Storage stability

| Composition of dispersion | 1 | 2 | 3 | 4 | 5 | 6 | 7 | 8 | V1 | V2 |
|---|---|---|---|---|---|---|---|---|---|---|
| 1 week, 5° C. | +++ | +++ | +++ | +++ | +++ | +++ | +++ | +++ | 0 | 0 |
| 2 Weeks, 5° C. | +++ | +++ | +++ | +++ | +++ | +++ | +++ | +++ | 0 | 0 |
| 4 Weeks, 5° C. | +++ | +++ | +++ | +++ | +++ | +++ | +++ | +++ | 0 | 0 |
| 6 Weeks, 5° C. | +++ | +++ | +++ | +++ | +++ | +++ | +++ | +++ | 0 | 0 |
| 1 Week, 20° C. | +++ | +++ | +++ | +++ | +++ | +++ | +++ | +++ | 0 | 0 |
| 2 Weeks, 20° C. | +++ | +++ | +++ | +++ | +++ | +++ | +++ | +++ | 0 | 0 |
| 4 Weeks, 20° C. | +++ | +++ | +++ | +++ | +++ | +++ | +++ | +++ | 0 | 0 |
| 6 Weeks, 20° C. | ++ | ++ | ++ | + | ++ | + | + | ++ | 0 | 0 |
| 1 Week, 40° C. | +++ | +++ | +++ | +++ | +++ | +++ | +++ | +++ | 0 | 0 |
| 2 Weeks, 40° C. | +++ | +++ | +++ | +++ | +++ | +++ | +++ | +++ | 0 | 0 |
| 4 Weeks, 40° C. | ++ | + | ++ | ++ | ++ | ++ | ++ | ++ | 0 | 0 |
| 6 Weeks, 40° C. | + | + | ++ | + | + | + | + | + | 0 | 0 |

In contrast to the two comparative formulations, which lost their stability after only 1 week at 5° C., all of the formulations according to the invention were completely stable over at least 4 weeks and showed losses only with storage times of 6 weeks at 40° C.

The invention claimed is:

1. Stable dispersions, containing
   (a) 50 to 80% by weight of perfume oils,
   (b) 10 to 30% by weight of encapsulated fragrances, and
   (c) 0.01 to 0.1% by weight of nonionic polymers of the type of the hydrophobically modified hydroxyalkyl guar compounds,
   with the proviso that the components (a)-(c) add up to 100% by weight together with water and optionally further auxiliaries and additives.

2. Dispersions as claimed in claim 1, wherein the perfume oils (component a) are selected from the group consisting of pine oil, citrus oil, jasmine oil, patchouli oil, rose oil, muscatel-sage oil, camomile oil, clove oil, melissa oil, mint oil, cinnamon leaf oil, lime blossom oil, juniper berry oil, vetiver oil, olibanum oil, galbanum oil, labdanum oil, orange blossom oil, neroli oil, orange peel oil and sandalwood oil and mixtures thereof.

3. Dispersions as claimed in claim 1, wherein the fragrances (component b) are selected from the group consisting of synthetic or natural esters, ethers, aldehydes, ketones, alcohols, hydrocarbons, acids, carbonic acid esters, aromatic hydrocarbons, aliphatic hydrocarbons, saturated and unsaturated hydrocarbons and mixtures thereof.

4. Dispersions as claimed in claim 1, wherein the fragrances (component b) are present in a capsule, the coating material of which is selected from the group consisting of melamine-formaldehyde resins and coacervates of anionic and cationic monomers and/or polymers and mixtures thereof.

5. Dispersions as claimed in claim 1, wherein said dispersions are in triphasic form.

6. Method for forming the stabilized aqueous dispersions of claim 1, comprising adding component (c) to an aqueous dispersion of components (a) and (b).

7. Cosmetic preparations containing the dispersions as claimed in claim 1.

8. Detergents and cleaning agents containing the dispersions as claimed in claim 1.

9. Method for the production of cosmetic preparations as well as detergents and cleaning agents, comprising adding the dispersions as claimed in claim 1 to the same.

* * * * *